US009877934B2

(12) United States Patent
Azam et al.

(10) Patent No.: US 9,877,934 B2
(45) Date of Patent: Jan. 30, 2018

(54) THERAPY FOR LEUKEMIA

(71) Applicants: Mohammad Azam, Mason, OH (US); Meenu Kesarwani, Mason, OH (US)

(72) Inventors: Mohammad Azam, Mason, OH (US); Meenu Kesarwani, Mason, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 132 days.

(21) Appl. No.: 14/048,806

(22) Filed: Oct. 8, 2013

(65) Prior Publication Data
US 2014/0031356 A1 Jan. 30, 2014

Related U.S. Application Data

(63) Continuation-in-part of application No. PCT/US2012/034359, filed on Apr. 20, 2012.

(60) Provisional application No. 61/477,853, filed on Apr. 21, 2011.

(51) Int. Cl.
*A61K 31/506* (2006.01)
*A61K 31/12* (2006.01)
*A61K 31/135* (2006.01)
*A61K 31/045* (2006.01)
*A61K 31/517* (2006.01)
*A61K 45/06* (2006.01)

(52) U.S. Cl.
CPC .......... *A61K 31/135* (2013.01); *A61K 31/045* (2013.01); *A61K 31/12* (2013.01); *A61K 31/506* (2013.01); *A61K 31/517* (2013.01); *A61K 45/06* (2013.01)

(58) Field of Classification Search
CPC .... A61K 31/506; A61K 31/12; A61K 31/135; A61K 31/045
See application file for complete search history.

(56) References Cited

U.S. PATENT DOCUMENTS

| 7,045,523 | B2* | 5/2006 | Tauchi | 514/252.18 |
| 8,318,815 | B2* | 11/2012 | Huang et al. | 514/731 |
| 2004/0127470 | A1* | 7/2004 | Masferrer | A61K 31/00 514/165 |
| 2006/0189543 | A1 | 8/2006 | Rosenbloom | |
| 2008/0207532 | A1* | 8/2008 | Huang | A61K 31/09 514/25 |
| 2009/0311702 | A1 | 12/2009 | Shak et al. | |
| 2010/0184779 | A1 | 7/2010 | Hughes | |
| 2011/0118298 | A1 | 5/2011 | Fritz et al. | |
| 2014/0031356 | A1 | 1/2014 | Azam et al. | |

FOREIGN PATENT DOCUMENTS

| WO | 2010/108058 A2 | 9/2010 |
| WO | 2010/108058 A3 | 9/2010 |
| WO | 2010/124283 A2 | 10/2010 |
| WO | 2011/014825 A2 | 2/2011 |

OTHER PUBLICATIONS

Henkes et al. (ther Clin Risk Manag (2008)4(1); 163-187.*
Mahon,Hematology 2012; 122-128.*
Drug Ther Perspect. 2000;16(10).*
International Search Report and Written Opinion PCT/US2012/034359, dated Nov. 29, 2012 (10 pages).
Extended European Search Report comprised of Supplementary European Search Report and the European Search Opinion PCT/US2012/034359, dated Oct. 10, 2014 (9 pages).
Azam et al. Anticipating Clinical Resistance to Target-Directed Agents the BCR-ABL Paradigm. Mol Diag Ther 10 (2006) 67-76.
Nardi et al. Mechanisms and implications of imatinib resistance mutations in BCR-ABL. Curr Opin Hematology 11 (2004) 35-43 and 1 page Figure 1.
Knight et al. Features of Selective Kinase Inhibitors. Chemistry & Biology 12 (2005) 621-637.
Shi et al. Triptolide Inhibits Bcr-Abl Transcription and Induces Apoptosis in STI571-resistant Chronic Myelogenous Leukemia Cells Harboring T3151 Mutation. Clin Cancer Res 15 (2009) 1686-1697.
Nabavi et al. Curcumin and Liver Disease: from Chemistry to Medicine. Comprehensive Reviews in Food Science and Food Safety 13 (2014) 62-77.
International Preliminary Report on Patentability PCT/US2012/034359, dated Oct. 22, 2013 (7 pages).
Aikawa et al. "Treatment of arthritis with a selective inhibitor of c-Fos/activator protein-1," Nature Biotechnology, vol. 26, No. 7 (2008), pp. 817-823.
Park et al., "Inhibition of fos-jun-DNA complex formation by dihydroguaiaretic acid and in vitro cytotoxic effects on cancer cells," Cancer Letters, vol. 127 (1998), pp. 23-28.
Padhye et al. Fluorocurcumins as Cyclooxygenase-2 Inhibitor: Molecular Docking, Pharmacokinetics and Tissue Distribution in Mice. Pharmaceutical Research, vol. 26, No. 11 (2009), pp. 2438-2445.
Padhye et al. New Difluoro Knoevenagel Condensates of Curcumin, Their Schiff Bases and Copper Complexes as Proteasome Inhibitors and Apoptosis Inducers in Cancer Cells. Pharmaceutical Research, vol. 26, No. 8 (2009), pp. 1874-1880.
International Search Report and Written Opinion PCT/US2015/33269, dated Aug. 19, 2015, 8 pages.
Bakan, Ahmet, et al.; "Toward a Molecular Understanding of the Interaction of Dual Specificity Phosphatases with Substrates: Insights from Structure-Based Modeling and High Throughput Screening"; Current Medicinal Chemistry, 15;.pp. 2536-2544 (2008).

(Continued)

*Primary Examiner* — Shirley V Gembeh
(74) *Attorney, Agent, or Firm* — Thompson Hine LLP

(57) ABSTRACT

A pharmaceutically acceptable composition and method for leukemia therapy in a patient in need of such therapy. The composition contains, as the only active agents, the combination of (a) an inhibitor of c-Fos, (b) an inhibitor of Dusp-1, and (c) an inhibitor of BCR-ABL tyrosine kinase. The composition is administered to the patient in a dosing regimen for a period sufficient to provide therapy for leukemia.

20 Claims, 23 Drawing Sheets

(56) References Cited

OTHER PUBLICATIONS

Nunes-Xavier, Caroline, et al.; "Dual-Specificity MAP Kinase Phosphatases as Targets of Cancer Treatment"; Anti-Cancer Agents in Medicinal Chemistry, 11; pp. 109-132 (2011).

Doddareddy, M. R., et al.; "Targeting Mitogen-Activated Protein Kinase Phosphatase-1 (MKP-1): Structure-Based Design of MKP-1 Inhibitors and Upregulators"; Current Medicinal Chemistry, 19; pp. 163-173 (2012).

Rios, Pablo et al.,; "Dual-Specificity Phosphatases as Molecular Targets for Inhibition in Human Disease"; Antioxidants & Redox Signaling; vol. 20, No. 14; DOI: 10.1089/ars2013.5709; pp. 2251-2274 (2014).

Korhonen, Riku, et al.; "Mitogen-Activated Protein Kinase Phosphatase 1 as an Inflammatory Factor and Drug Target"; Basic & Clinical Pharmacology & Toxicology, 114; DOI: 10.1111/bcpt12141; pp. 24-36 (2014).

He, Rong-jun, et al.; "Protein tyrosine phosphatases as potential therapeutic targets"; Acta Pharmacological Sinica, 35; pp. 1227-1246.

Kundu, Suman, et al.; "Tyrosine Phosphatase Inhibitor-3 Sensitizes Melanoma and Colon Cancer to Biotherapeutics and Chemotherapeutics"; Preclinical Development; Molecular Cancer Therapeutics 9 (8); DOI: 10.1158/1535-7163.MCT-10-0159; pp. 2287-2296 (2010).

Molina et al. Zebrafish chemical screening reveals an inhibitor of Dusp6 that expands cardiac cell lineages. Nature Chemical Biology 5 (2009) 680-687.

Huang et al. Suppression of c-Jun / AP-1 activation by an inhibitor of tumor promotion in mouse fibroblast cells. Proc. Natl. Acad. Sci. USA 88 (1991) 5292-5296.

Park et al. Inhibition of fos-jun-DNS complex formation by dihydroguaiaretic acid and in vitro cytotoxic effects on cancer cells. Cancer Letters 127 (1998) 23-28.

Purwana et al. Induction of Dual Specificity Phosphatase 1 (DUSP1) by Gonadotropin-Releasing Hormone (GnRH) and the Role for Conadotropin Subunit Gene Expression in Mouse Pituitary Gonadotroph LbetaT2 Cells. Biology of Reproduction 82 (2010) 352-362.

Azam et al. Mechanisms of Autoinhibition and STI-571/Imatinib Resistance Revealed by Mutagenesis of BCR-ABL. Cell 112 (2003) 831-843.

International Preliminary Report on Patentability for PCT/US2015/033269, dated Dec. 6, 2016 (6 pages).

\* cited by examiner

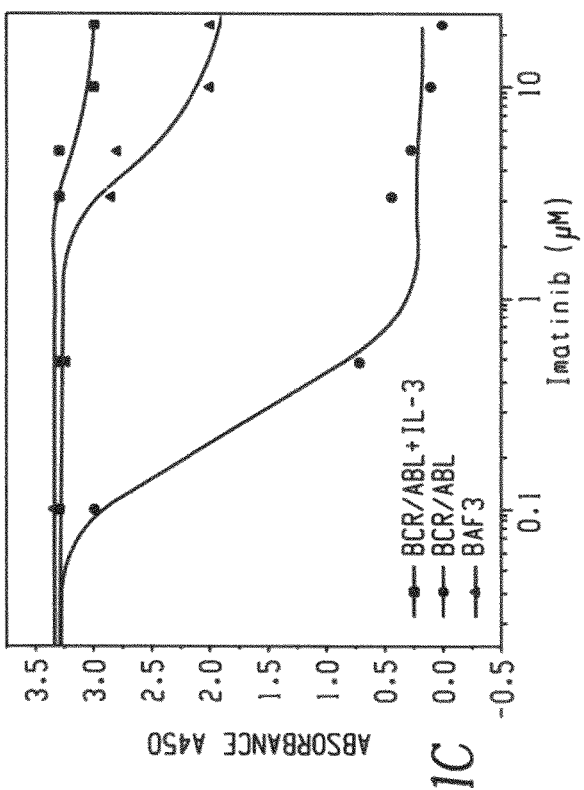
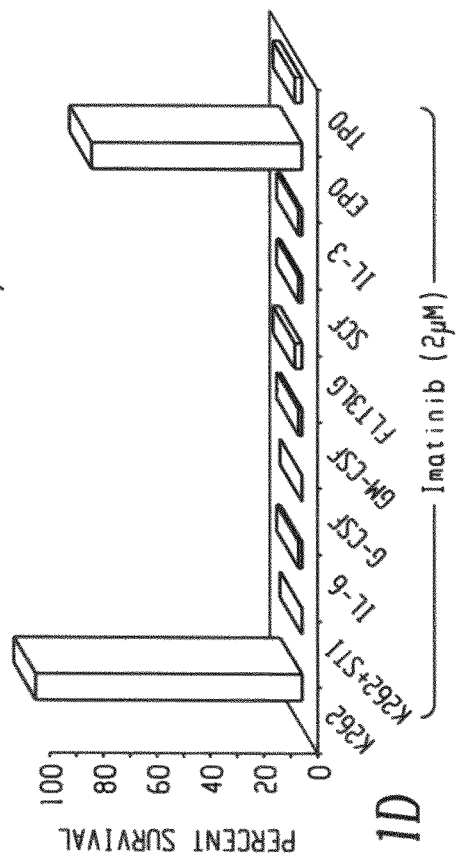
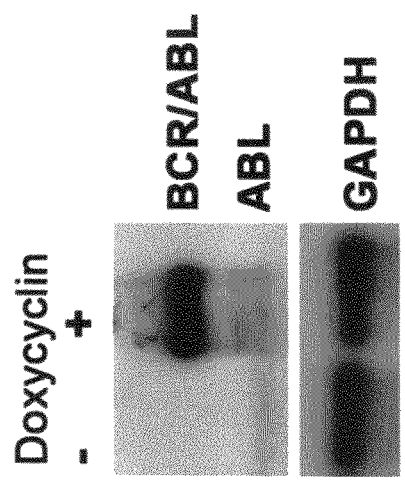
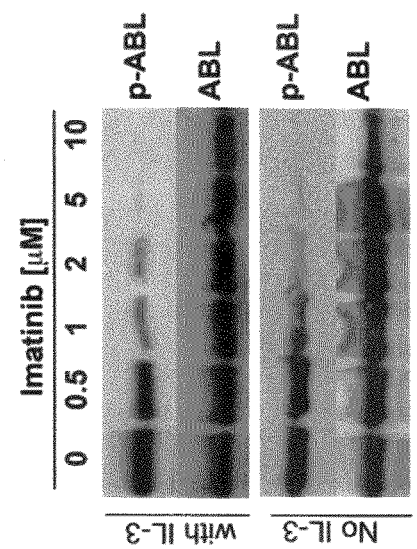
Fig. 1A
Fig. 1B
Fig. 1C
Fig. 1D

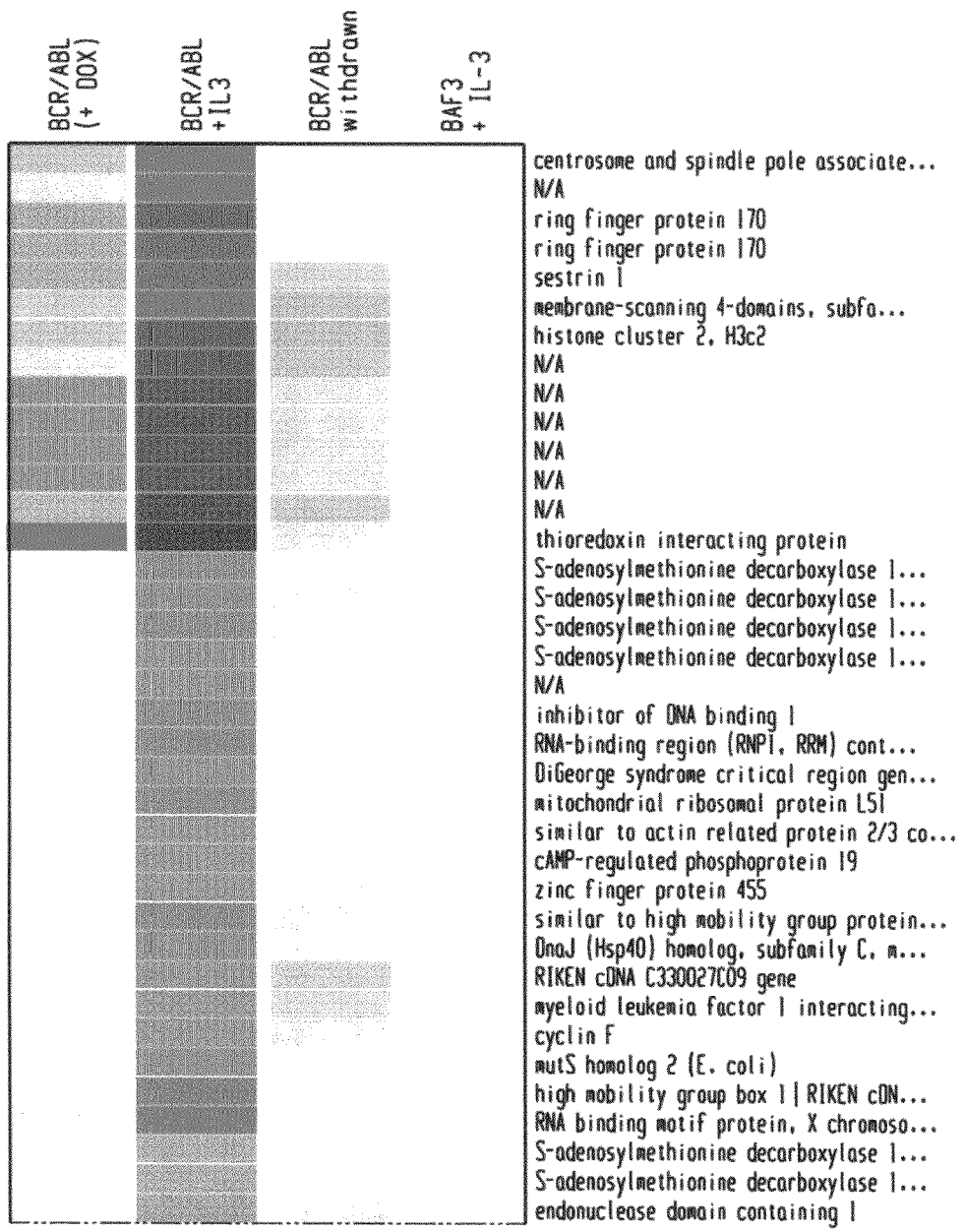
Fig. 2A1

MATCH TO FIG.2A1 slingshot homolog 2 (Drosophilia)
DEP domain containing 1a
DEP domain containing 1a
N/A
olfactory receptor 1252
N/A
N/A
RIKEN cDNA 2810021G02 gene
N/A
splicing factor, arginine/serine-rich 3(...
Gen homolog 1, endonuclease (Drosop...
similar to PDZ binding kinase (predicted)
RINKEN cDNA 5730449L18 gene
RINKEN cDNA 1810054D07 gene
polymerase (DNA directed), epsilon 2 (...
zinc finger protein 294
RINKEN cDNA D030056L22 gene
transmembrane protein 69
ATPase type 13A3
polymerase (DNA directed), alpha 1
centromere protein H
similar to multi sex combs CG12058-PA
N/A
centromere protein H
proteoglycan 3
similar to protein phosphatase 1, catal...
N/A
Shc-SH2-domain binding protein 1
fatty acid synthase
U3A small nuclear RNA
gastric inhibitory polypeptide receptor
MAX dimerization protein 1
zinc funger CCCH type containing 12C
syntaxin 11
N/A
interleukin-1 receptor-associated kina...
N/A

MATCH TO FIG.2A3

Fig. 2A2

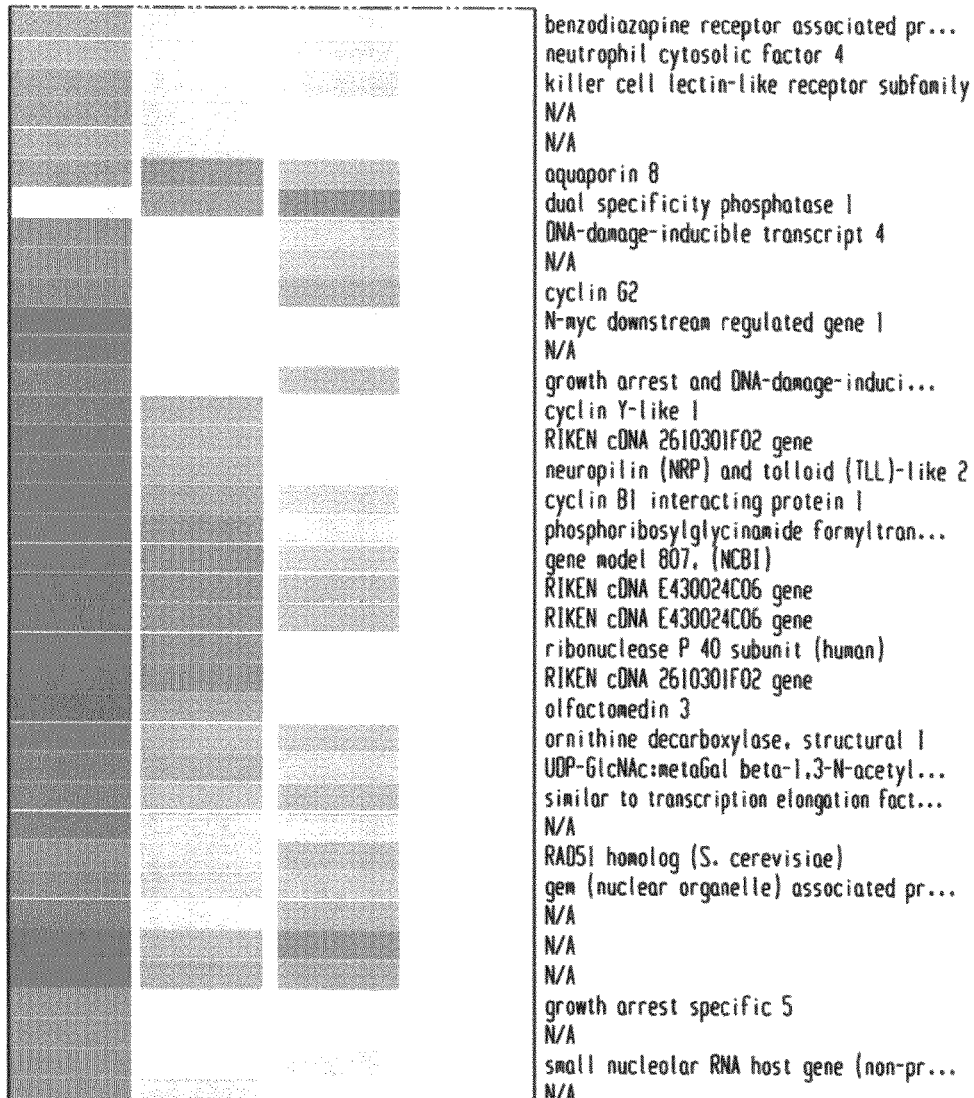
Fig. 2A3

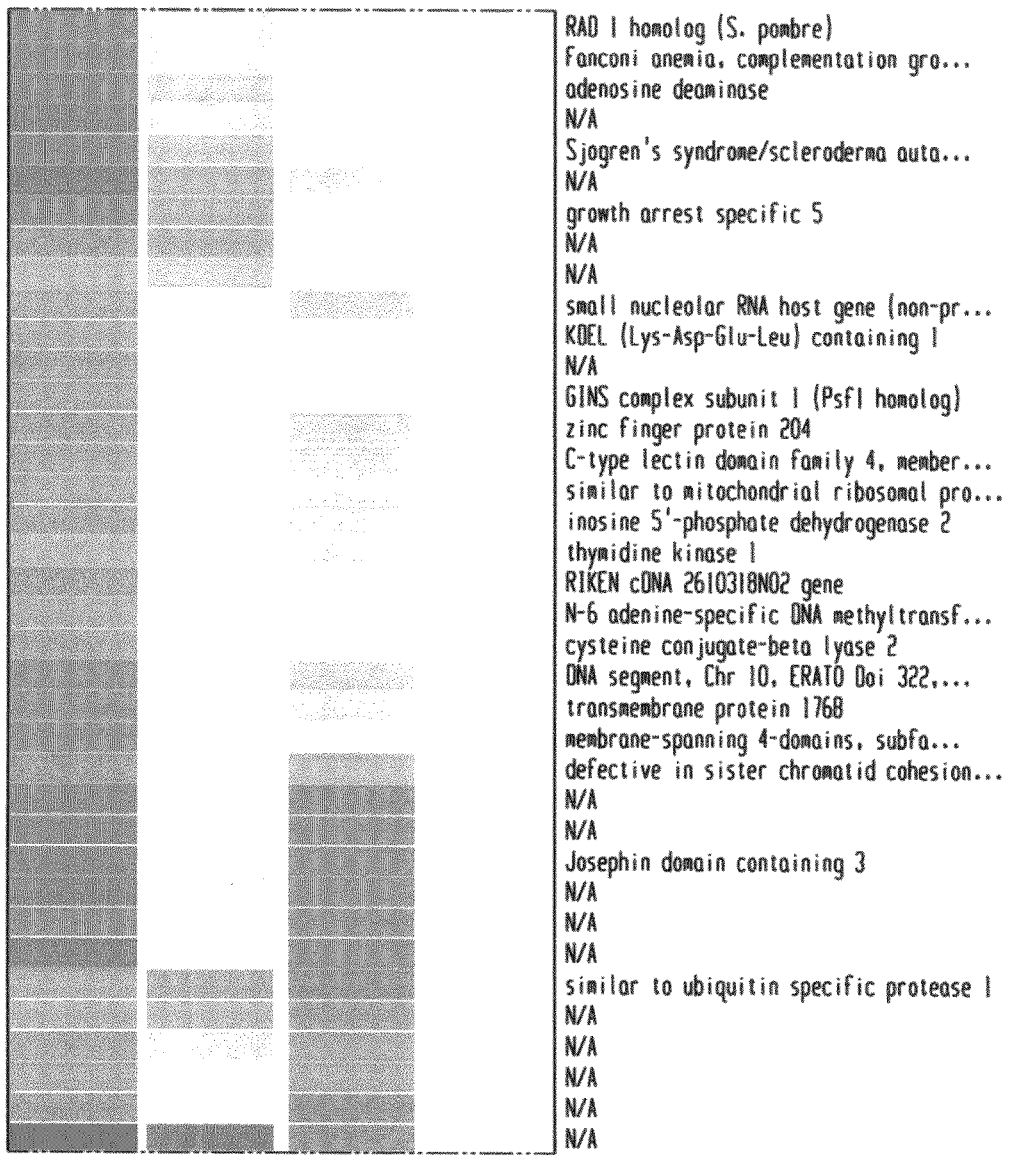
Fig. 2A4

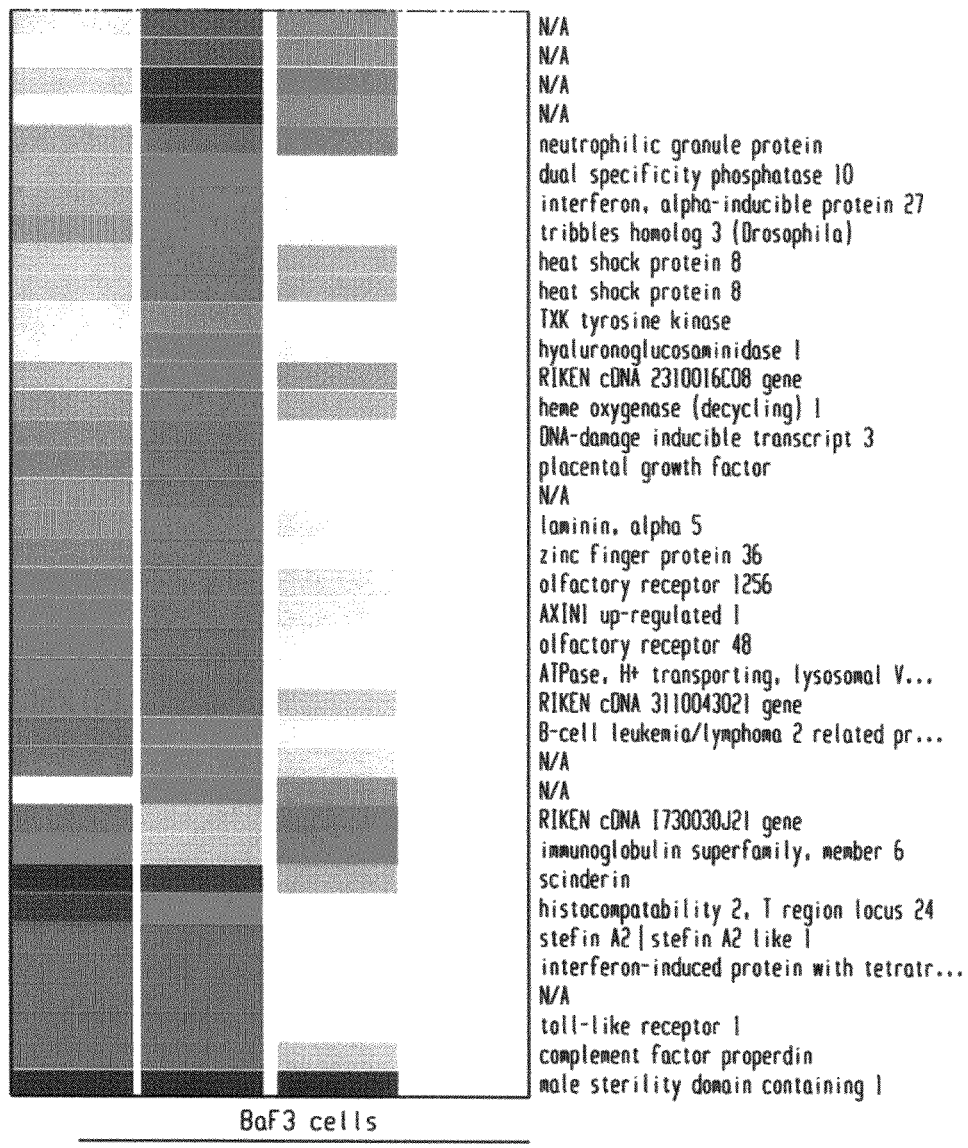
Fig. 2A5

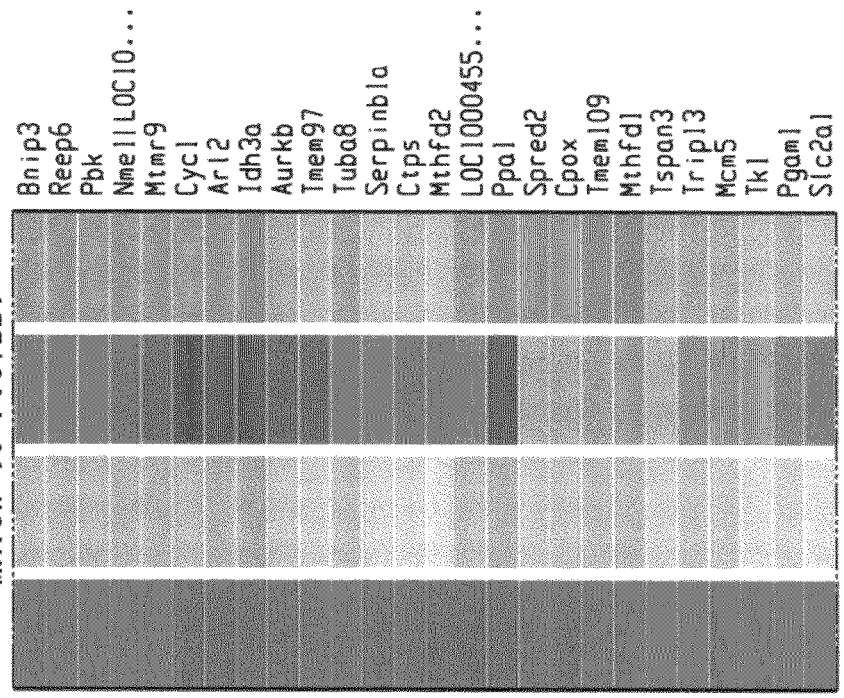
Fig. 2B2
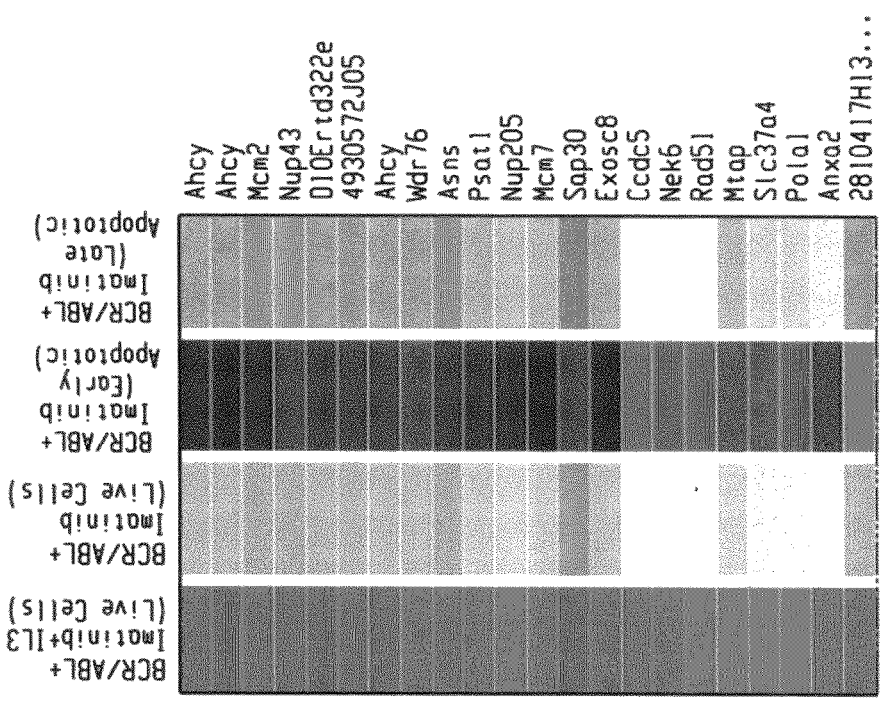
Fig. 2B1

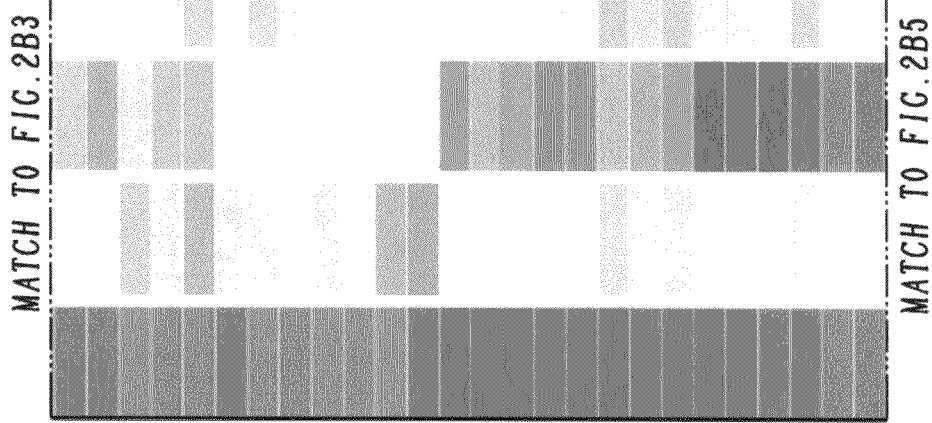
Fig. 2B3
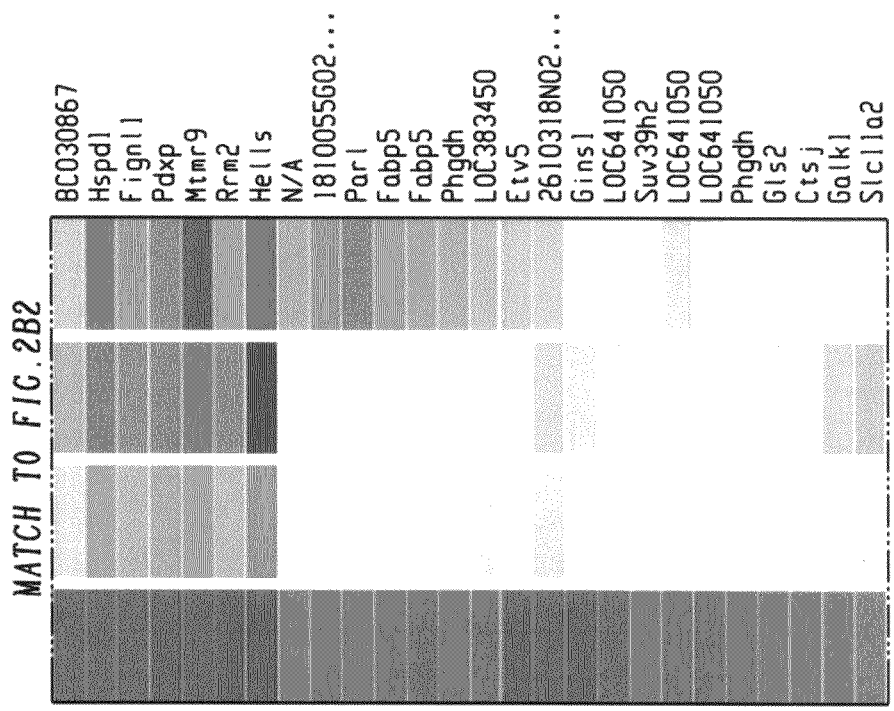
Fig. 2B4

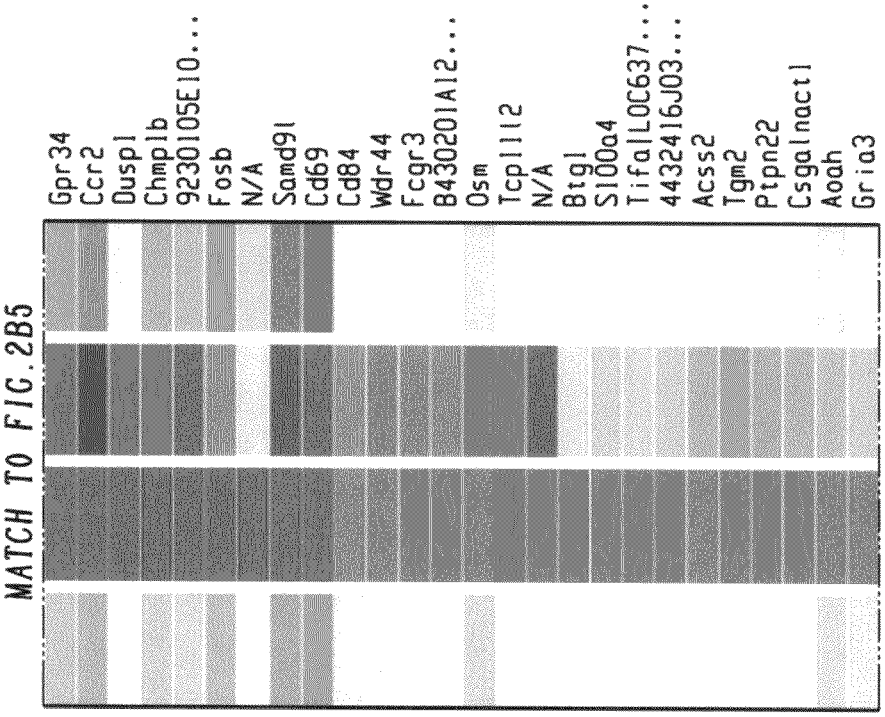
Fig. 2B5
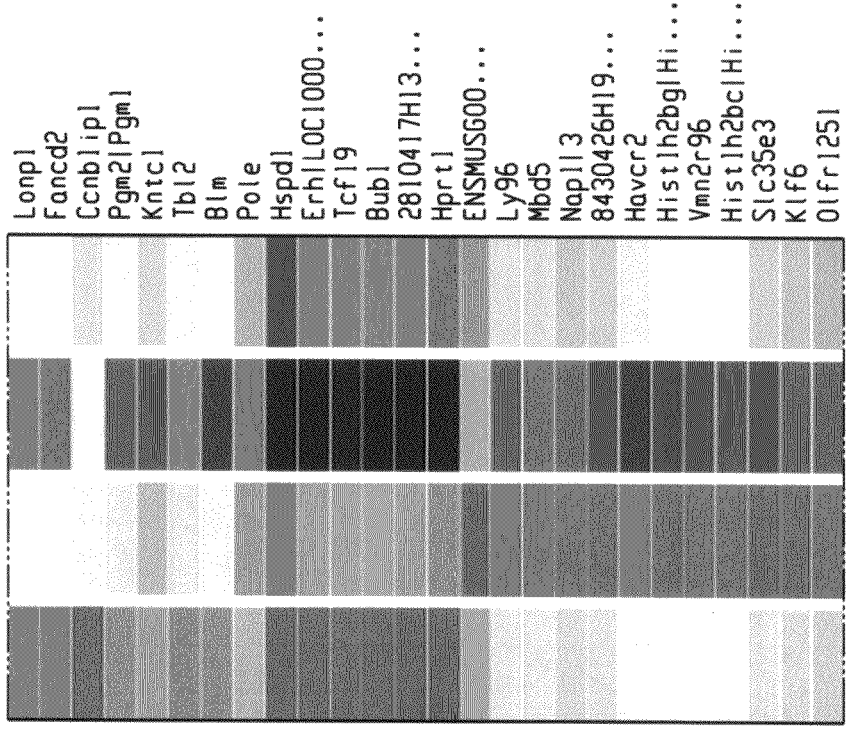
Fig. 2B6

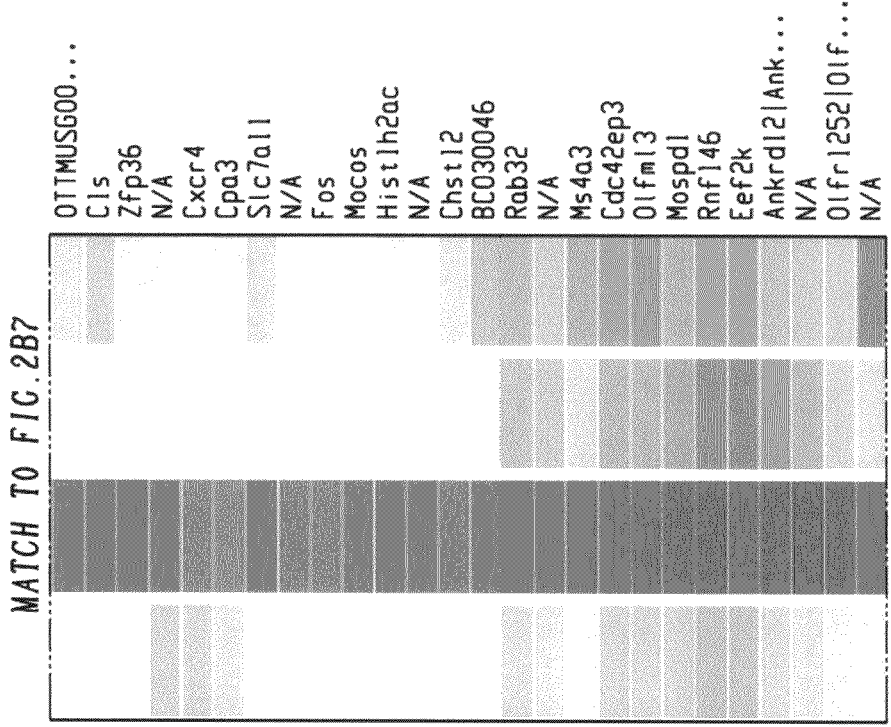
Fig. 2B8
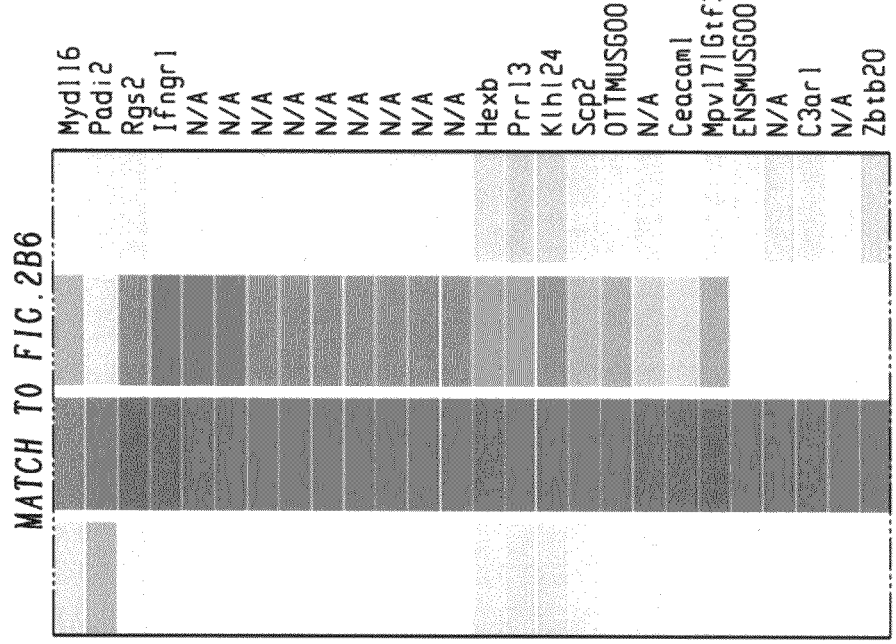
Fig. 2B7

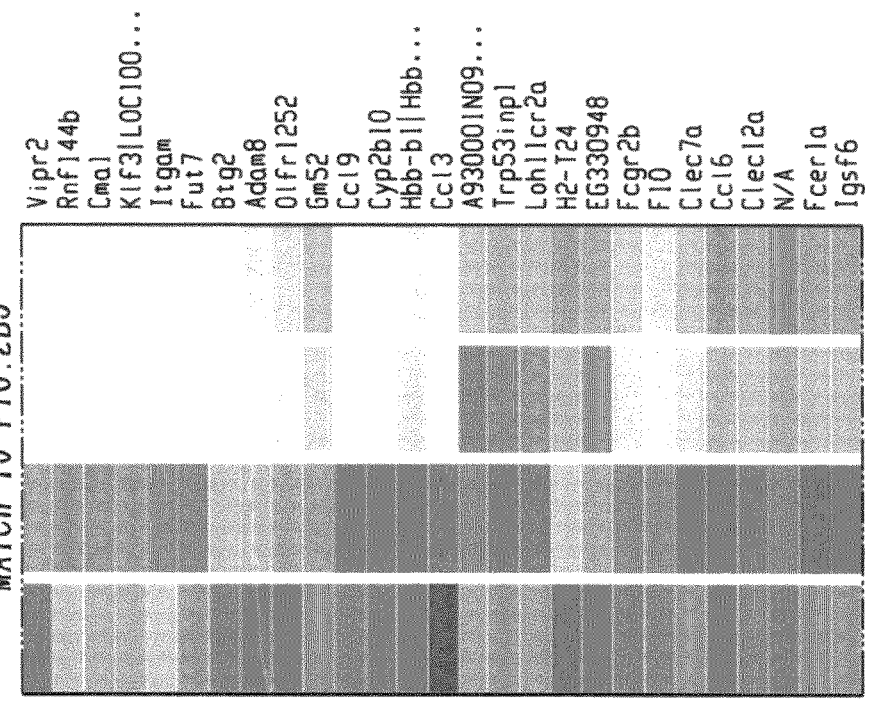
Fig. 2B10
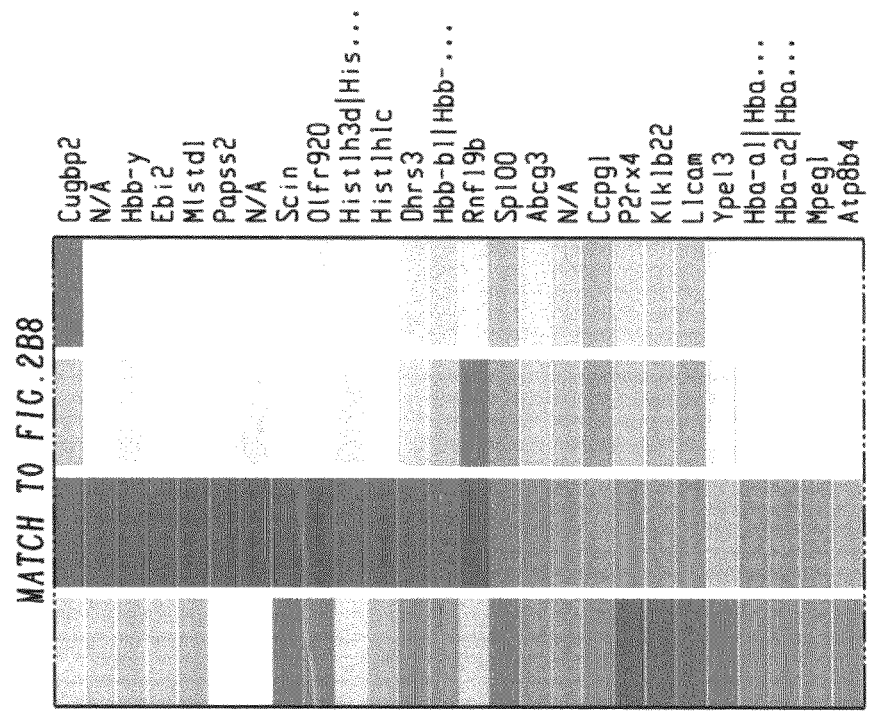
Fig. 2B9

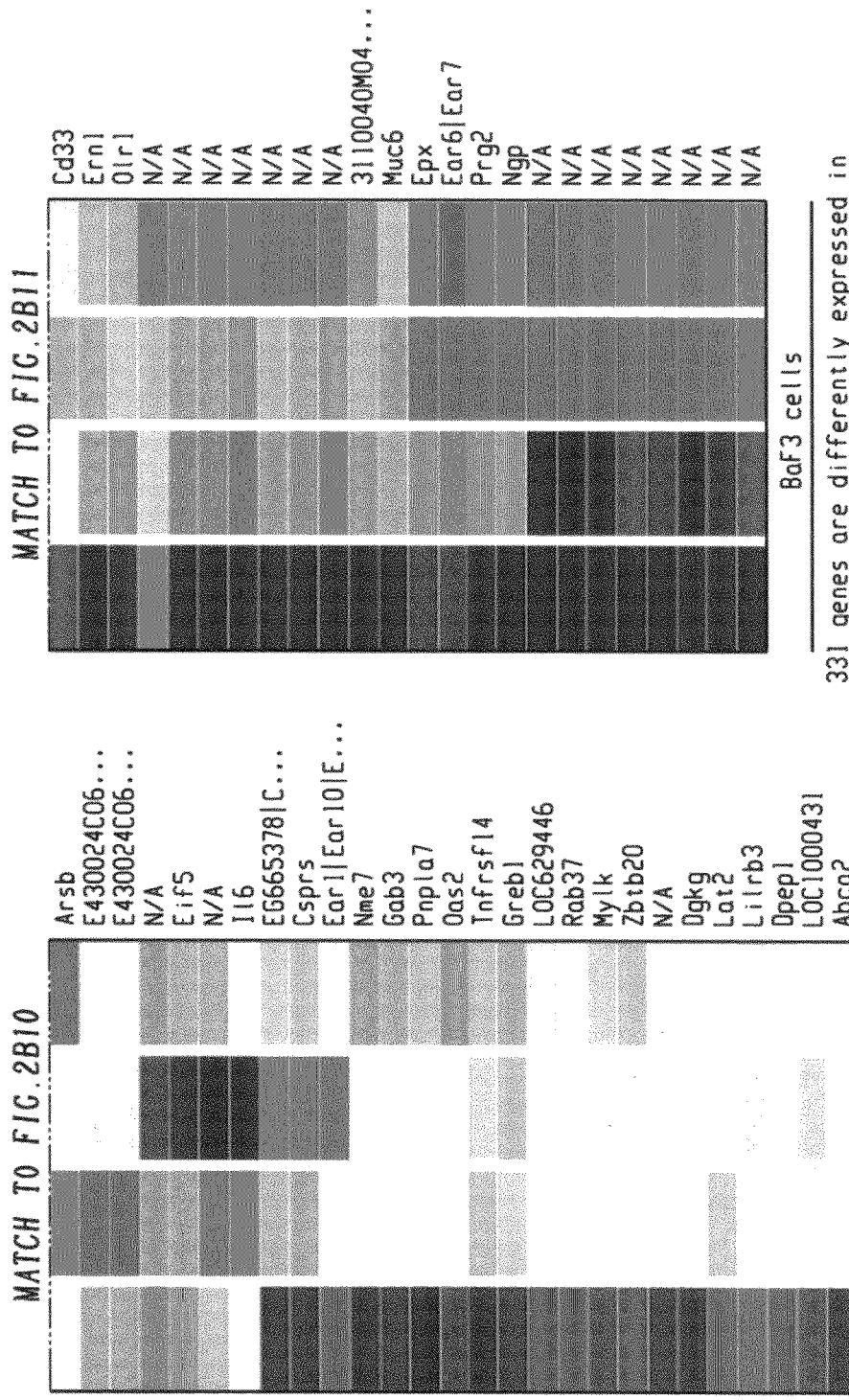
Fig. 2B12
Fig. 2B11

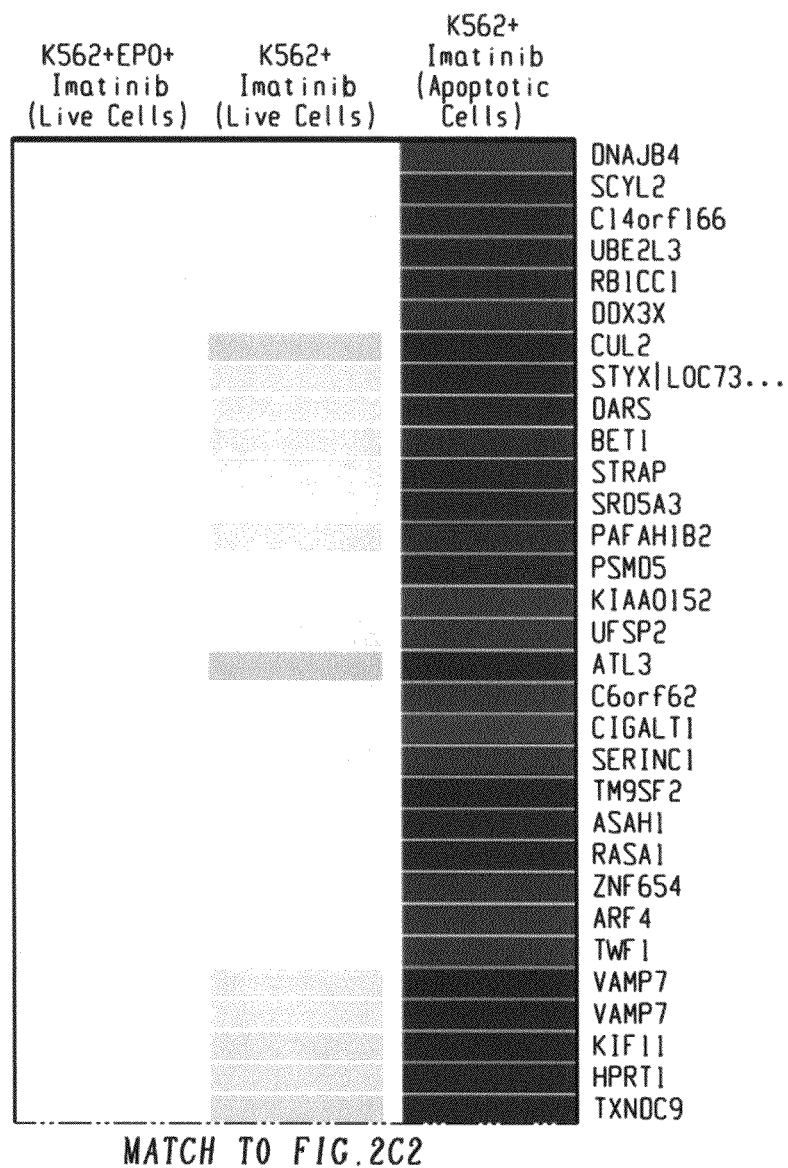
Fig. 2C1

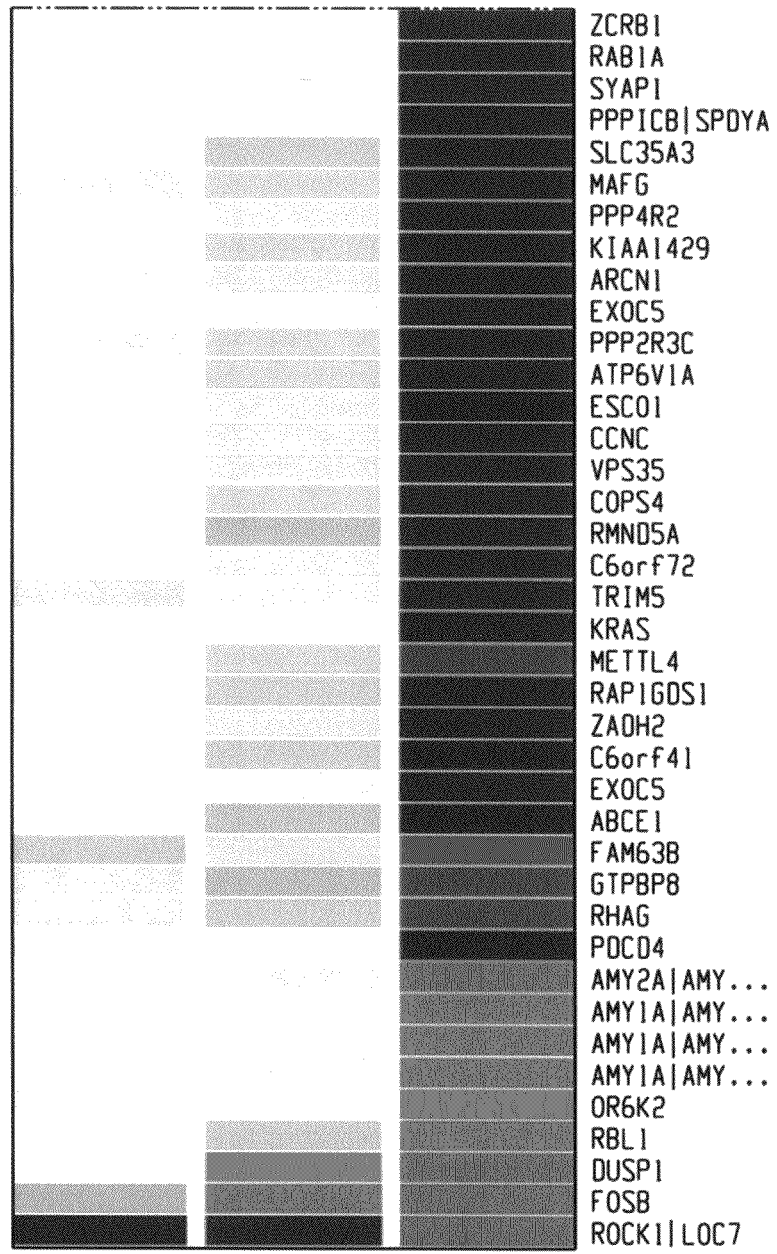
Fig. 2C2

Fig. 2D1

Before Treatment | One week of Imatinib Treatment

HLA-E
YPEL5
BAALC
IL10RA
PTPRO
CLK1
IRF7
NLRP1
IRF1
BCL2A1
TNFAIP2
TYROBP
GBP2
EVI2B
SORL1
SELL
PROM1
GLIPR1
SORL1
ZNF185
GLIPR1
STAG3L1
CRHBP
ZNF91
ANPEP
CSF3R
TSC22D3
BTG2
RHOB
BCL6
ORM1 /// OR...
TCN1
KLF2
GPR109B
IGHM
IGHM
JUNB
NFKBIA
TNFAIP3
GADD45B
ZFP36
TNFAIP3

MATCH TO FIG. 2D2

MATCH TO FIG.2D1

PTGS2
ID2
ID2
CXCR4
HIST2H2BE
HIST2H2AA3...
HIST2H2AA3...
DUSP1
MS4A3
MMP9
S100P
LCN2
ARG1
CD24
GOS2
BHLHE40
DDIT4
STK17B
IER3
HES1
IL8
DDIT3
RGS1
CXCL2
JUN
KLF10
EGR1
FOS
FCGR3B
MNDA
IL8RB
SERPINA1
FPR1
CSTA
CFD
ELA2
AZU1
LTF
S100A8
S100A9
S100A12
IL8
MAFF

CD34+cells
from CMLpts.

Fig. 2D2

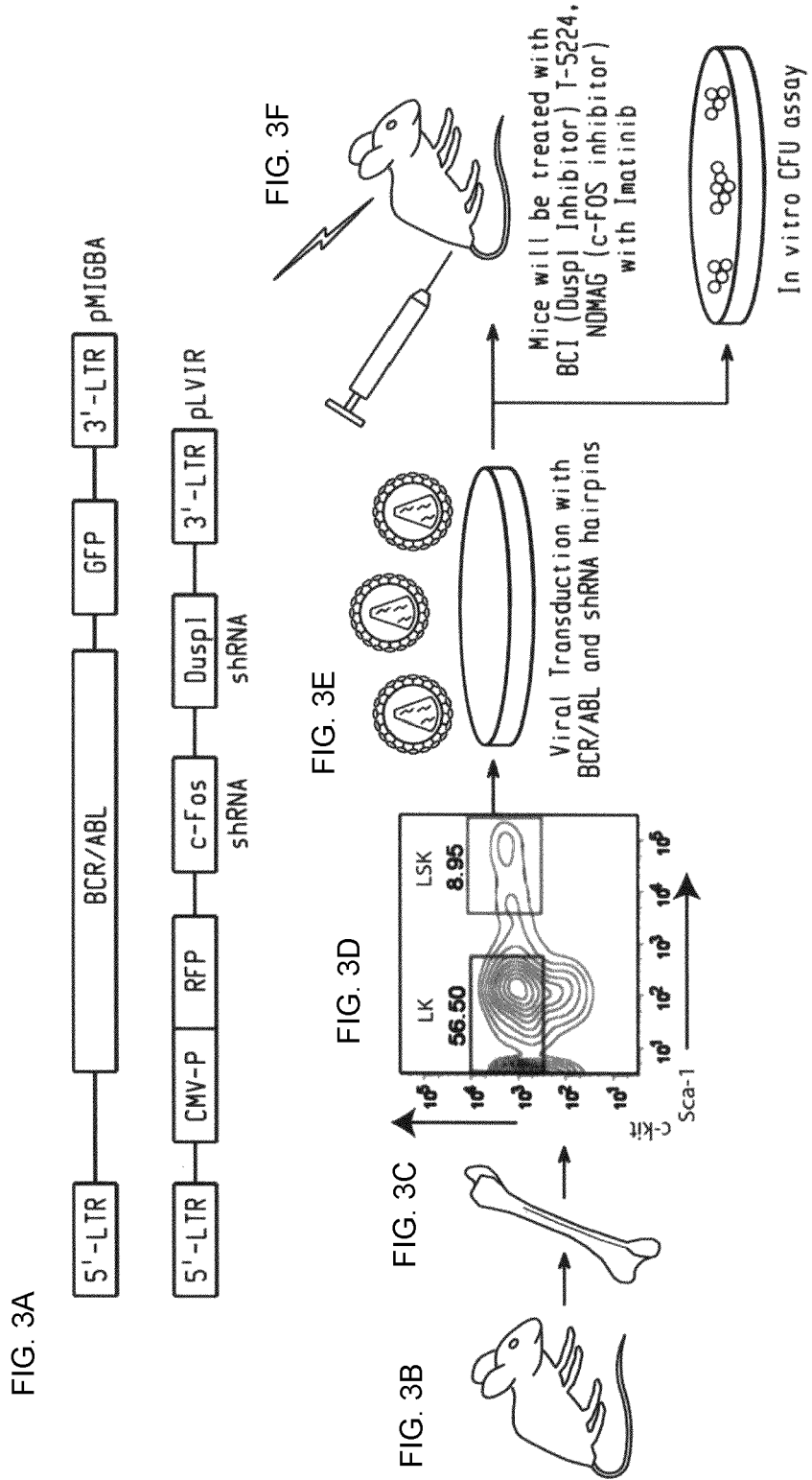

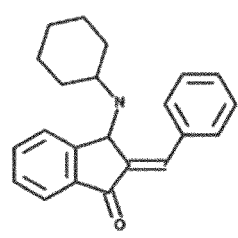
BCI
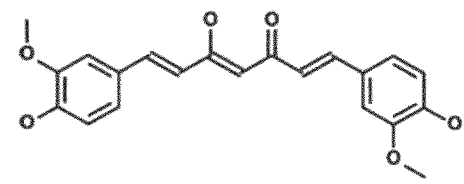
Curcumin
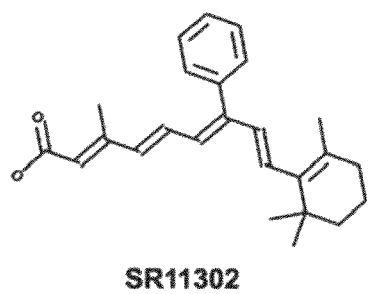
SR11302
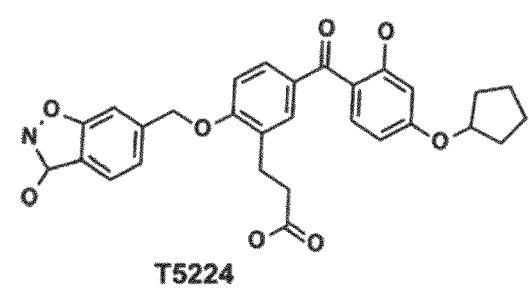
T5224
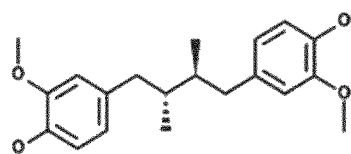
Dihydroguaiaretic acid
(DGA)
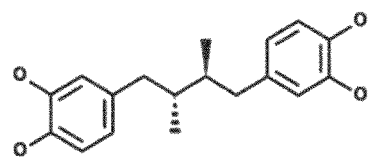
Nordihydroguaiaretic acid
(NDGA)
Fig. 4

THERAPY FOR LEUKEMIA

This application is a continuation-in-part of co-pending International Application Serial No. PCT/US2012/034359 filed Apr. 20, 2012, which claims priority to U.S. Provisional Application Ser. No. 61/477,853 filed Apr. 21, 2011, each of which is expressly incorporated by reference herein in its entirety.

A composition and method of using the composition to effect therapy for leukemia. In one embodiment, therapy is for chronic myelogenous leukemia. In one embodiment, therapy is for acute myelogenous leukemia. Therapy for targeting cancer stem cells and other leukemias are included. As used herein, therapy and treatment are broadly defined to encompass disease cure, or any lessening of disease presence, prevalence, severity, symptoms, etc.

In one embodiment, the composition contains at least one biocompatible excipient and, as its only active agents, the combination of at least one inhibitor of c-Fos, at least one inhibitor of Dusp-1, and at least one inhibitor of BCR-ABL tyrosine kinase. In one embodiment, the composition contains at least one biocompatible excipient and, as its only active agents, the combination of one inhibitor of c-Fos, one inhibitor of Dusp-1, and one inhibitor of BCR-ABL tyrosine kinase. In either of the aforementioned embodiments, the inhibitor may inhibit the gene and/or the protein, i.e., the c-Fos inhibitor may inhibit the c-Fos gene and/or protein, the Dusp-1 inhibitor may inhibit the Dusp-1 gene and/or protein, and the BCR-ABL tyrosine kinase inhibitor may inhibit the BCR-ABL tyrosine kinase gene and/or protein. Such inhibitors include commercially available inhibitors and inhibitors under development. Small molecule inhibitors, such as curcumin, difluorinated curcumin (DFC), [3-{5-[4-cyclopentyloxy)-2-hydroxybenzoyl]-2-[(3-hydroxy-1,2-benzisoxazol-6-yl) methoxy]phenyl}propionic acid] (T5224, Roche), nordihydroguaiaretic acid (NDGA), dihydroguaiaretic acid (DHGA), [(E,E,Z,E)-3-methyl-7-(4-methylphenyl)-9-(2,6,6-trimethyl-1-cyclohexen-1-yl)-2,4,6,8-nonatetraenoic acid (SR11302, Tocris Biosciences), (E)-2-benzylidene-3-(cyclohexylamino)-2,3-dihydro-1H-inden-1-one (BCI), TPI-2, TPI-3, triptolide, Imatinib mesylate (Gleevec™), Nilotinib, Dasatinib and Ponatinib, are encompassed. In one embodiment, inhibitors of c-Fos used in the composition are curcumin, difluorinated curcumin (DFC), [3-{5-[4-(cyclopentyloxy)-2-hydroxybenzoyl]-2-[(3-hydroxy-1,2-benzisoxazol-6-yl) methoxy]phenyl}propionic acid] (T5224, Roche), nordihydroguaiaretic acid (NDGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302, Tocris Biosciences). In one embodiment, inhibitors of Dusp-1 are (E)-2-benzylidene-3-(cyclohexylamino)-2,3-dihydro-1H-inden-1-one (BCI), also known as NSC 150117, TPI-2, TPI-3, and triptolide. In one embodiment, inhibitors of BCR-ABL tyrosine kinase are Imatinib mesylate (Gleevec™), Nilotinib, Dasatinib and Ponatinib. In one embodiment, the composition administered is curcumin, BCI, and Imatinib. In one embodiment, the composition administered is difluorinated curcumin (DFC), BCI, and Imatinib. In one embodiment, the composition administered is NDGA, BCI, and Imatinib. In one embodiment, the composition is T5224, BCI, and Imatinib. In one embodiment, the composition is administered to the patient at a concentration of 2 grams per day to 8 grams per day, inclusive, of the c-Fos inhibitor, 100 mg per day to 600 mg per day, inclusive, of BCI, and 400 mg to 800 mg per day, inclusive, of the BCR-ABL tyrosine kinase inhibitor Imatinib mesylate (Gleevec™). The composition is alkaline, about pH 8.5. In one embodiment, the composition is administered to the patient for 30 days. The composition may be administered by any route including but not limited to intravenous administration. The composition is preferably administered intravenously, orally, intramuscularly, transdermally, and/or intraperitoneally. Any biocompatible excipient may be used in the inventive composition, as known to one skilled the art. Biocompatible excipients include, but are not limited to, buffers, tonicity agents, pH modifying agents, preservatives, stabilizers, penetrant enhances, osmolality adjusting agents, etc. In one embodiment, the composition components are administered as individual components by the same route of administration or by different routes of administration, with administration of each component or components at substantially the same time. In one embodiment, the composition components are formulated into a cocktail, using methods known by one skilled in the art.

Cancer can be treated by identifying a molecular defect. This was demonstrated with chronic myelogenous leukemia (CML), the first cancer to be associated with a defined genetic abnormality, BCR-ABL, and the success of the small molecule tyrosine kinase inhibitor (TKI) Imatinib.

Despite Imatinib's efficacy in treating CML patients, it failed to provide a curative response because it preferentially targets the differentiated and dividing cells, therefore causing relapse upon Imatinib withdrawal. The major limitation to develop curative therapy is lack of understanding of the molecular and patho-physiological mechanisms driving cancer maintenance, progression, mechanisms of therapeutic response and relapse. As in the case of CML, differentiated and dividing cells undergo apoptosis following the acute inhibition of BCR-ABL, termed "oncogene addiction". In contrast, leukemic stem cells (LSCs) do not show similar response. Given the intrinsic resistance of LSCs to TKI therapy in CML, understanding the molecular mechanisms of oncogene addiction in therapeutically responsive cells would allow strategies to target the LSCs.

More specifically, the BCR-ABL tyrosine kinase inhibitor Imatinib improved the survival of patients with leukemia, but did not eliminate leukemia initiating cells (LIC). This suggested that LICs were not addicted to BCR-ABL.

The inventive method demonstrates that the down-regulation of c-Fos and Dusp-1 mediate BCR-ABL addiction, and that inhibition of c-Fos and Dusp-1 together induces apoptosis in BCR-ABL positive cells following Imatinib treatment. The combination of c-Fos and Dusp-1 inhibition has no effect on survival and apoptosis of parental BaF3 cells, a hematopoietic cell line; Dusp-1 and c-Fos knockout mice are viable and survive without any serious phenotype, suggesting that these targets are suitable for therapeutic development. The inventive method assessed effectiveness of targeted c-Fos and Dusp-1 inhibition in LICs for Imatinib response. Assessment included both genetic (shRNA) and pharmacological inhibitors. This provided a basis for clinical application of a composition containing Imatinib, a c-Fos inhibitor, and a Dusp-1 inhibitor to target leukemic cells, such as CML initiating cells and AML initiating cells.

Chronic myelogenous leukemia (CML) is a slow-growing bone marrow cancer resulting in overproduction of white blood cells. CML is caused by the abnormal phosphorylation of cellular proteins by a deregulated enzyme, BCR-ABL tyrosine kinase. A small molecule inhibitor Imatinib mesylate (Gleevec™) was developed to block aberrant BCR-ABL tyrosine kinase activity. Gleevec™ was a major breakthrough in fighting cancer; Imatinib treatment not only revolutionized CML management but also paved the way for development of tyrosine kinase inhibitor therapy for other diseases.

Imatinib treatment is not curative. Many patients develop resistance despite continued treatment and some patients simply do not respond to treatment. Evidence suggests that a subset of cancer cells, termed "cancer stem cells", drive tumor development and are refractory to most treatments. In other words, cancer cells that respond to the drug treatment are critically dependent upon uninterrupted oncogene function, are "addicted to oncogene", whereas cancer stem cells are not dependent or addicted to oncogene. Thus, eradication of these cancer stem cells is a critical part of any successful anti-cancer therapy.

CML has long served as a paradigm for generating new insights into the cellular origin, pathogenesis and improved approaches to treating many types of human cancer. Cancer stem cells in CML serve as safe reservoir to develop therapeutic resistance. This emphasizes the need for new agents that effectively and specifically target CML stem cells.

The inventive method targeted the CML stem cells to produce curative therapies that do not require lifelong treatments. The inventive method will serve as a paradigm to investigate other disease models and may help in devising improved strategies for developing curative therapeutics.

Oncogene addiction is the "Achilles' heel" of many cancers. The major limitation to develop curative cancer therapy has been a lack of understanding of the molecular and patho-physiological mechanisms driving cancer maintenance, progression, and mechanisms of therapeutic response and relapse. In 2002, Bernard Weinstein proposed the concept that cancer cells acquire abnormalities in multiple oncogenes and tumor suppressor genes. Inactivation of a single critical gene can induce cancer cells to differentiate into cells with normal phenotype, or to undergo apoptosis, which is popularly known as "oncogene addiction". This dependence or addiction for maintaining the cancer phenotype provides an Achilles heel for tumors that can be exploited in cancer therapy. In CML, differentiated and dividing cells undergo apoptosis following acute inhibition of BCR-ABL, and are thus "BCR-ABL addicted". However, CML LICs do not show a similar response and are thus not "addicted" to BCR-ABL function.

The clinical activity of Imatinib in multiple disease settings, together with numerous cancer cell line studies demonstrating an apoptotic response to drug treatment, suggests that clinical responses are likely to reflect oncogene dependency on activated kinases for their survival. Likewise, EGFR inhibitors in the treatment of lung cancer represents another example of oncogene addiction that has yielded clinical success in a subset of patients with advanced disease that are otherwise refractory to conventional chemotherapy treatment. Mutations in the kinase domain of EGFR are found in a small subset of non-small cell lung cancers (NSCLC), and clinical responses to EGFR inhibitors, Gefitinib and Erlotinib, have been well correlated with such mutations. Further, cancer genome sequencing data have also highlighted the likely role of "kinase addiction" in a variety of human cancers, e.g., activation of MET, BRAF, FGFR2, FGFR3, ALK, AURK and RET kinase in various different malignancies. Underscoring the importance of oncogene addiction is the fact that in all of these kinase-mediated malignancies, acute inactivation of the mutated kinase by either genetic or pharmacological means results in growth inhibition or tumor cell death. In sum, the potential and importance of oncogene addiction in molecularly targeted cancer therapy highlights the fact that activated oncogenes, especially kinases, represent cancer culprits that frequently contribute to a state of oncogene dependency.

Cell culture models, genetically engineered mice, and clinical testing of targeted drugs support a widespread role for oncogene addiction in tumor cell maintenance and response to acute oncoprotein inactivation. The precise mechanism by which cells acquire dependency on a single pathway or activated protein is not clear in most cases, but multiple theories have nonetheless been put forth; signaling network dysregulation, synthetic lethality genetic streamlining, and oncogenic shock. However, experimental evidence to prove these models is generally lacking, and it is unlikely that a single mechanism accounts for the numerous reported experimental findings that appear to represent examples of oncogene dependency, and therefore it represents an important area of investigation. Additionally, mechanisms governing oncogene addiction may vary according to the cellular and extracellular context.

Given the intrinsic resistance of LICs to TKI therapy in CML, a detailed understanding of oncogene dependency in therapeutically responsive cells permits engineering the therapeutically resistant cells LICs to achieve drug sensitivity. mRNA and miRNA expression studies were thus performed in BCR-ABL addicted and non-addicted cells to identify the candidate gene(s) mediating the drug response.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-D demonstrate that growth factor signaling in leukemic cells abrogates BCR-ABL dependence.

FIGS. 2A1-F demonstrate that AP-1 transcription factor c-Fos and dual specificity phosphatase-1 mediate BCR-ABL addiction.

FIGS. 3A-F schematically demonstrate in vitro and in vivo evaluation of c-Fos and Dusp-1 to induce BCR-ABL addiction in leukemic stem cells (LSCs).

FIG. 4 shows the chemical structure of selected inhibitors.

Figure 2E:
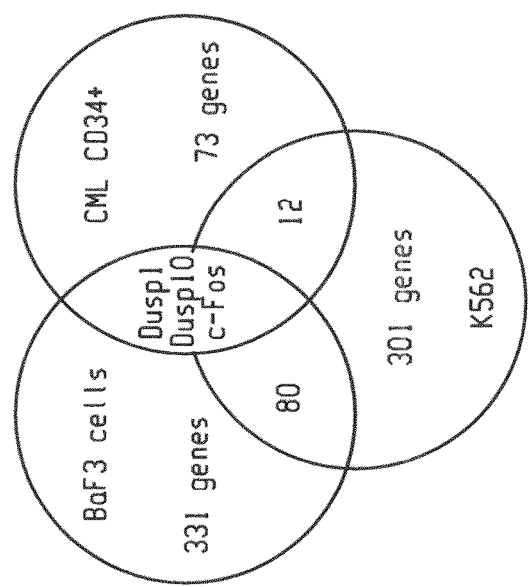

Chronic myelogenous leukemia (CML) initiating cells are intrinsically resistant to small-molecule kinase inhibitors. This discovery has prompted interest in developing strategies to more effectively target CML initiating cells. One line of activity involves global gene expression analyses. Another line of activity involves identification of downstream partners essential for maximum BCR-ABL oncoprotein activity. These have reinforced early evidence of activation of the JAK/STAT, PI3K/AKT, RAS/MAPK and NFKB pathways in the primitive CML LIC. These studies have also identified differentially expressed genes involved in regulation of DNA repair, cell cycle control, cell adhesion, homing, transcription factors, and drug metabolism. None of these studies identified potential therapeutic targets useful to eradicate the CML LIC. Failure to identify such a target may be due to the fact that, in many studies, expression profiling was done either on total bone-marrow samples or CD34+ fractionated cells. Apart from constitutional BCR-ABL expression that causes genetic instability in time dependent fashion, CD34+ fractionated cells carry a good degree of heterogeneity in itself. Thus, variations in patients sample and use of a heterogeneous cell population obscured identification of meaningful targets. Based on these observations, knowing the mechanisms of oncogene addiction in Imatinib sensitive cells wilt permit engineering of CML LIC to achieve sensitivity for kinase inhibitors.

In one embodiment, the BCR-ABL tyrosine kinase inhibitor is at least one of Imatinib (Novartis), Nilotinib (Novartis), Dasatinib (BMS), and Ponatinib (Ariad). In one embodiment, the BCR-ABL tyrosine kinase inhibitor is Imatinib.

In one embodiment, the Dusp-1 inhibitor is at least one of BCI, TPI-2, TPI-3, and triptolide. In one embodiment, the Dusp-1 inhibitor is BCI.

In one embodiment, the c-Fos inhibitor is at least one of curcumin, difluorinated curcumin (DFC), T5224, nordihydroguaiaretic acid (NDGA), dihydroguaiaretic acid (DHGA), and SR11302. In one embodiment, the c-Fos inhibitor is curcumin. In one embodiment, the c-Fos inhibitor is difluorinated curcumin (DFC). In one embodiment, the c-Fos inhibitor is NDGA. In one embodiment, the c-Fos inhibitor is T5224.

An unbiased mRNA expression profiling was performed using BAF3 cells, which requires IL-3 for survival, expressing the BCR-ABL tyrosine kinase under a Tet-R responsive promoter that renders them IL-3-independent. BaF3 cells were used because it is homogeneous in terms of gene expression, and because BCR-ABL dependence is reversible. Specifically, in the presence of exogenous IL-3, BAF3 cells no longer depend on BCR-ABL for survival, as shown in FIG. 1.

More specifically, FIG. 1 shows that growth factor signaling in leukemic cells abrogates the BCR-ABL dependence. FIG. 1A shows conditional expression of BCR-ABL in BaF3 cells; without doxycycline there is no expression of BCR-ABL in BaF3 cells. FIG. 1B is a Western blot showing the kinase activity of BCR-ABL at different concentrations of inhibitor. This demonstrated that IL-3 had no effect on mediated kinase inhibition. FIG. 1C shows a dose response curve for Imatinib on BAF3-BCR-ABL cells, where squares are BCR-ABL+IL-3, circles are BCR-ABL, and triangles are BAF3. This demonstrated that Imatinib was no longer effective when cells were grown with IL-3. FIG. 1D shows cell proliferation assays showing the abrogation of BCR-ABL addiction K562 cells when grown with erythropoietin (EPO), while other hematopoietic cytokines did not have a significant effect.

This biology is reminiscent of CD34+ CML stem cell behavior. The data were obtained on freshly made BaF3 cells expressing BCR-ABL conditionally, because long-term expression of BCR-ABL in any cell causes severe genomic instability and permanent irreversible changes in gene expression. This likely would exacerbate problems identifying the critical gene or genes involved in BCR-ABL addiction.

To define the differential expression of gene(s) in BCR-ABL addicted and non-addicted conditions, expression analysis was performed using total RNA from BaF3 cells, BaF3 cells expressing BCR-ABL conditionally in the presence and absence of exogenously added IL-3 (FIG. 2A1) and BaF3-BCR-ABL cells treated with Imatinib in the presence and absence of IL-3 (FIG. 2B1).

AP-1 transcription factor c-Fos and dual specificity phosphatase-1 mediated the BCR-ABL addiction. Comparative analysis of gene expression from these two data sets would allow identification of the sets of genes involved in BCR-ABL addiction, and identified 331 genes that were differently expressed in these conditions. Given BCR-ABL addiction in K562 cells and attenuation of addiction by erythropoietin, similar gene expression analysis in K562 cells would permit sorting out the false positives and may corroborate the data sets. Expression profiling of K562 cells identified 301 differently expressed genes; about one third of the genes are common to the gene list of BCR-ABL-BaF3 (FIG. 2B1). To narrow the list to identify clinically significant candidate genes, these data sets were compared with the expression profiling of CD34$^+$ cells from CML patients before and after Imatinib treatment. Only three genes, Dusp-1, Dusp-10, and c-Fos, were down regulated in BCR-ABL addicted cells, while they were upregulated to 3-5 fold in non-addicted cells. This suggested their role in BCR-ABL dependence. The role of these three genes in mediating BCR-ABL addiction were evaluated; specifically, whether their down-regulation in non-addicted cells would sensitize them to Imatinib induced apoptosis. c-Fos, Dusp-1 and Dusp-10 were knocked down using shRNA hairpin, and cell survival analysis was performed in the presence of 5 µM Imatinib, which typically kills addicted cells in 24 hrs at this concentration, and IL-3. Dusp-1 and c-Fos knockdown alone induced 30% and 40% sensitivity to Imatinib, respectively. Dusp-10 knock down did not show any significant sensitivity to Imatinib. This suggested that double knock down of c-Fos and Dusp-1 may sensitize the BCR-ABL cells fully. To test this, instead of using shRNA mediated gene knock down of Dusp-1, a small molecule inhibitor that targets Dusp-I, BCI, was used. In cell proliferation assays, BaF3-BCR-ABL cells with c-Fos knockdown were fully sensitive to Imatinib when combined with BCI (FIG. 2F). The same combinations of drugs had no effect on BCR-ABL positive and parental BaF3 cells, highlighting the response specificity.

Figure 2F:
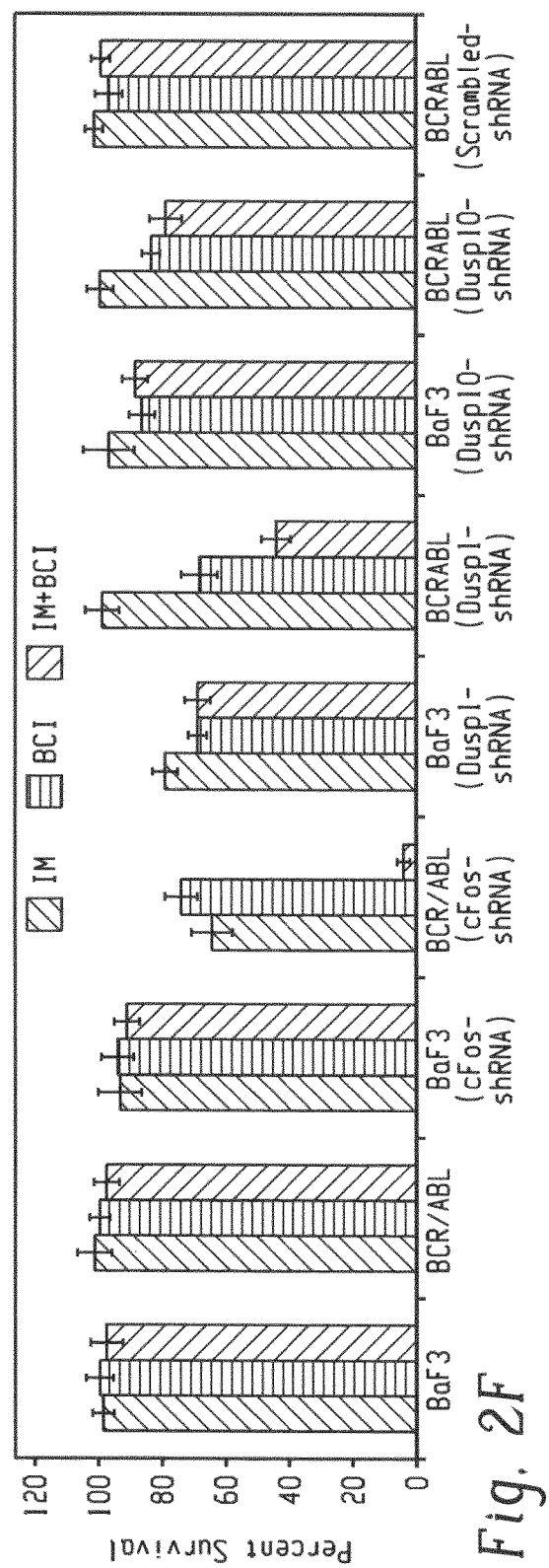
Figure 5:
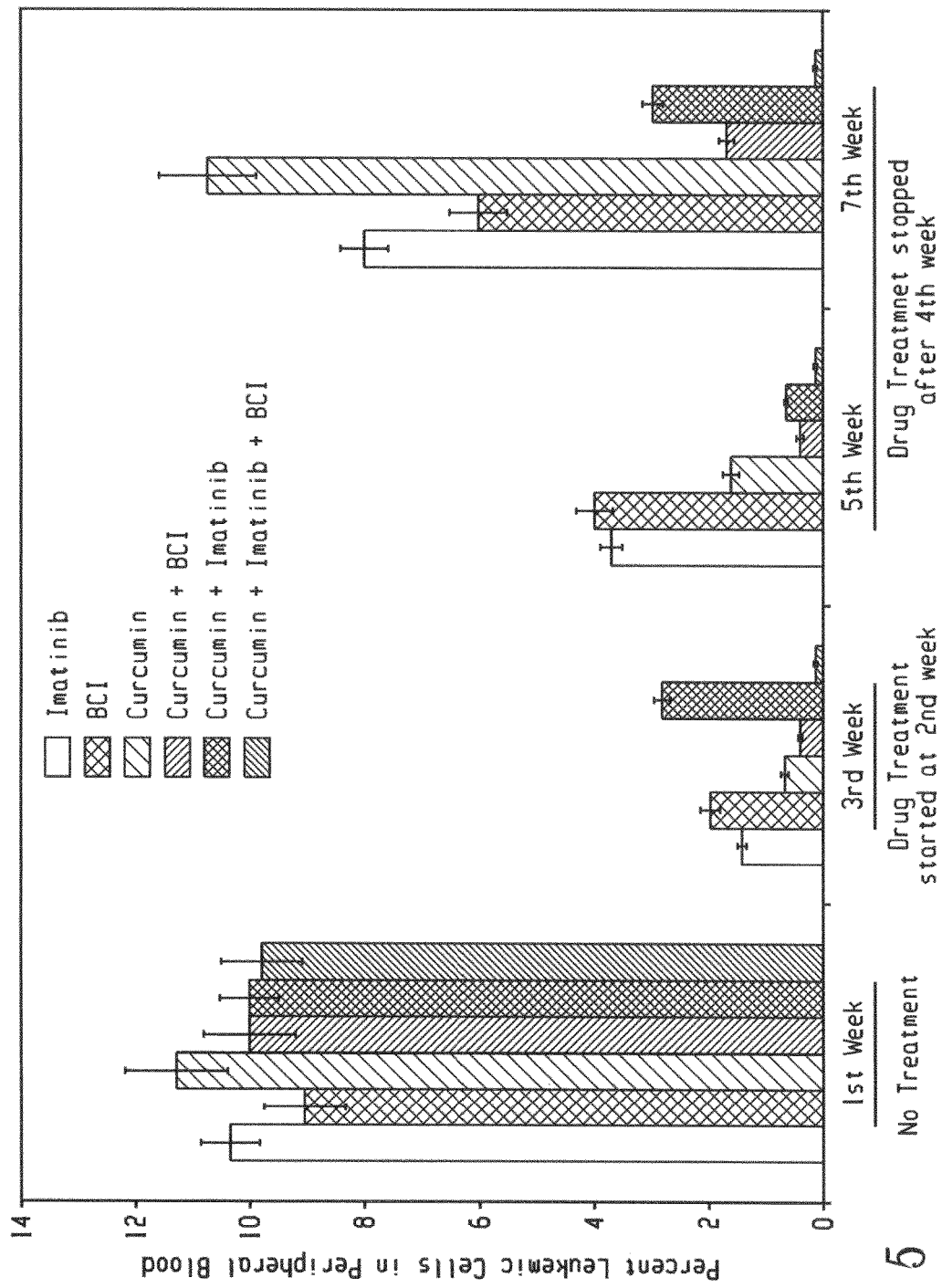
FIG. 5 demonstrates treatment effects for Imatinib, (E)-2-benzylidene-3-(cyclohexylamino)-2,3-dihydro-1H-inden-1-one (BCI), and curcumin separately and combined.

FIGS. 2A1-2A5 are a heat map of differential gene expression in BaF3 cells expressing the BCR-ABL grown with and without exogenously added IL-3. Expression of BCR-ABL was induced by adding doxycycline in the growth media. This expression profile was normalized with parental BaF3 cells grown with IL-3. This analysis identified 809 genes that were differently regulated by BCR-ABL in the presence of IL-3. FIGS. 2B1-2B12 are a heat map showing that 900 genes were differently expressed in the BCR-ABL-BaF3 cells treated with Imatinib in the presence and absence of IL-3. Cells treated with IL-3 and Imatinib are resistant to apoptosis and are represented as live cells; cells treated with Imatinib in the absence of IL-3 will apoptose. To identify the critical genes that mediates resistance or sensitivity to Imatinib in addicted cells, cells were separated into three distinct sub-populations: live, early-apoptotic, and late-apoptotic using Annexin V and propidium iodide staining. Comparing gene lists from A and B identified that 331 genes are common and are differently regulated. FIGS. 2C1-2C2 show expression profiling of K562 cells treated with Imatinib in the presence and absence of erythropoietin (EPO). This analysis identified 301 genes that were expressing differently in K562 cells. FIGS. 2D1-2D2 show expression profiling of CD34$^+$ positive cells from CML patients before and after one week of Imatinib treatment (gene set enrichment (GSE) 12211) which identified 87 genes that were differently expressed. FIG. 2E is a Venn diagram showing overexpression of three genes Dusp-1, Dusp-10, and c-Fos in BaF3 cells, K562, and CML-CD34+ cells. FIG. 2F is a cell proliferation assay of BCR-ABL cells expressing shRNA hairpins for c-Fos, DuspI and Dusp-10 was performed in the presence of IL-3 with 5 µM Imatinib and 1 µM of the Dusp-1 inhibitor (E)-2-benzylidene-3-(cyclohexylamino)-2,3-dihydro-1H-inden-1-one (BCI), alone or in combination. In each group of three, the top bar indicates Imatinib, the middle bar indicates BCI, and the lower bar indicates Imitinib+BCI. The results revealed that down regulation of c-Fos and Dusp-1 together mediated the BCR-ABL addiction.

Efficacy of Dusp-1 and c-Fos inhibition in mouse model of CML and CD34+ cells from CML patients was shown. The BCR-ABL tyrosine kinase inhibitor Imatinib improves the survival of patients but does not eliminate LICs. This suggested that these cells are not addicted to BCR-ABL. The data demonstrated that downregulation of c-Fos and Dusp-1 mediated BCR-ABL addiction. Inhibition of c-Fos and Dusp-1 together induced apoptosis in BCR-ABL positive cells following Imatinib treatment. The same combination has no effect on survival and apoptosis of parental BaF3 cells. Dusp-1 and c-Fos knockout mice were viable and survived without any serious phenotype, suggesting that these targets were suitable for therapeutic development. The effectiveness of c-Fos and Dusp-1 inhibition in LICs for Imatinib response was determined before making any therapeutic utility.

c-Fos and Dusp-1 were targeted using both genetic (shRNA) and pharmacological inhibitors to provide a basis for clinical application to target CML initiating cells. The retroviral bone marrow transduction transplantation model of BCR-ABL-induced CML was established. FIG. 3 shows schema for in vitro and in vivo evaluation of c-Fos and Dusp-1 to induce BCR-ABL addiction in LSCs. FIG. 3A shows retrovirus and lentivirus constructs for hematopoietic stem/progenitor transduction. FIGS. 3B, C and D show bone marrow harvesting and sorting of Kit+ cells. FIG. 3E shows viral transduction of K+L−S+ cells with pMIGBA and pL VIR viruses followed by cell sorting for doubly positive cells GFPIRFP cells. FIG. 3F shows that these doubly positive cells will be injected to mice followed with treatment by Imatinib alone and in combination with Dusp-1 and Fos inhibitors. CFU assays in the presence and absence of Imatinib, and also in combination with Dusp-1 and Fos inhibitors are performed.

Therapeutic response of Imatinib in LICs following the c-Fos and Dusp-1 knock down using shRNA overexpression was evaluated. As shown in FIG. 3, flow-sorted Kit+Lin−Sca1+ cells from C51BU6 mice were transduced with retroviruses expressing BCR-ABL-Ires-GFP and lentiviruses overexpressing shRNAs for c-Fos and Dusp-1 with RFP. The transduced cells were sorted again for GFP and RFP positivity. These doubly positive cells were used for in vitro and in vivo analysis. As a control, vector containing scrambled shRNA transduced cells and cells expressing the shRNA for Dusp-1 and Fos alone in the presence and absence of BCR-ABL were used. For each condition, 10 mice were injected through tail vein with $10^4$ sorted cells mixed with $5 \times 10^5$ RBC depleted total bone marrow. After seven days, mice were subjected to drug, Imatinib, BCI, treatments. To evaluate the effect of drug administration on apoptosis of stem cells in vivo, a set of leukemic mice were sacrificed on day 5 of treatment and apoptosis in the KLS population was measured by labeling with Annexin V and DAPI. For in vitro CFU assays, methylcellulose colonogenic assays are performed by plating $10^3$ sorted cells in 0.9% MethoCult (Stem Cell Technologies) with hematopoietic growth factors in the presence of Imatinib alone, BCI alone, and in combination of both inhibitors. Colonies (>100 µm) from primary cells are scored after 7-15 days. If good transduction efficiency is not achieved due to use of two different viruses, inducible transgenic ScI-tTaBCRIABL are used. BM cells are obtained from ScI-tTa-BCRABL-GFP mice 4 weeks after induction of BCR-ABL expression by tetracycline withdrawal, and a pure population of KLS/GFP-expressing cells are sorted by flow cytometry followed with viral transduction expressing shRNA hairpins for Dusp-1 and c-Fos. These transduced cells are subjected to in vitro and in vivo analysis.

Inhibition of c-Fos and Dusp-1 in primary CML CD34+ cells was shown to evaluate the inventive composition as a therapeutic agent on primary human samples. Quiescent CD34+ CML cells from chronic phase patients are known to be less sensitive than the bulk of the CD34+ leukemic cells to the cytotoxic effects of Imatinib inhibition in vitro. This quiescent population is enriched in CML stem cells (CD34+ CD38− cells), but also typically still contains large numbers of more mature CD34+CD38+ cells.

To determine the effect of c-Fos and Dusp-1 inhibition with Imatinib, Lin−CD34+CD38+ primitive CML stem cells were isolated followed with in vitro colony forming unit (CFU) assay. Additionally, 50,000 Lin−CD34+CD38− cells were grown in liquid culture with and without the growth factors IL-3, IL-6, G-CSF, Flt3-LG, SCF and EPO in the presence of Imatinib (alone), BCI (alone), and with all compounds in combination. After 72 hrs cells were stained with Annexin V and PI to analyze apoptosis. Clinical samples from CML patients were tested.

mRNA expression studies were performed in BCR-ABL addicted and non-addicted cells to identify the candidate gene or genes mediating drug response. Of several candidate genes, inhibition of Dual-specificity phosphatase-1 (Dusp-1) and c-Fos by ShRNA and/or small molecule inhibitors greatly sensitized the LSCs for Imatinib. This suggested intrinsic resistance of cancer stem cells could be targeted and may provide curative benefit.

To validate the role of Dusp-1 and c-Fos in Imatinib response and therapeutic targeting of leukemic stem cells in vivo, a bone marrow transduction transplantation model was used. Bone marrow cells from normal C57Bl/6 mice were transduced with BCR-ABL retroviruses expressing GFP and transferred to sub-lethally irradiated mouse hosts. Such mice develop a reproducible myeloproliferative disease similar to human CML. Treatment with BCR-ABL inhibitors Imatinib, Nilotinib and Dasatinib prolonged survival of these mice for 3-4 weeks and leukemic stem cells in these mice are resistant to therapy as in human subjects, suggesting kinase inhibitor therapy is not curative. Groups of mice (n=6) were treated with Imatinib at a dose of 100 mg/kg/day, BCI at a dose of 5 mg/kg/day targeting Dusp-1, and curcumin at a dose of 50 mg/kg/day targeting c-Fos by intraperitoneal injection. An identical dose of combination of drugs, Imatinib and BCI, Imatinib and curcumin, BCI and curcumin, and Imatinib and BCI and curcumin, were injected intraperitoneally. Drug treatments were started on day 8 following the bone marrow transplants. Leukemic burden in mice was assessed weekly by monitoring the GFP positive cells in peripheral blood using FACS.

As shown in FIG. 5. the combination of Imatinib, BCI and curcumin cured mice from CML. In FIG. 5, from left to right, the six bars in each of the four groups (1st week, 3rd week, 5th week, 7th week) are, in this order, Imatinib, BCI, curcumin, curcumin+BCI, curcumin+Imatinib, curcumin+ Imatinib+BCI. The histograms show the percentage of GFP positive cells from peripheral blood as leukemic burden in mice. Each histogram represented the average value of GFP positive cells from six mice. Single drug treatment, or a two drug combination treatment suppressed most leukemic cells, but there were residual leukemic cells in circulation at three weeks. However, a combination of Imatinib, BCI, and curcumin did not show any significant number of leukemic cells in circulation. Mice treated with the Imatinib, BCI and curcumin (the rightmost bar in each group) did not relapse following drug withdrawal. This result suggested these mice were cured from the disease.

A way to ascertain that there are no leukemic stem cells in mice is stop drug treatment and test for disease relapse. Any leukemic stem cells surviving in bone marrow will repopulate the disease, while curing the disease will fail to do so. Also as shown in FIG. 5, drug treatment was thus stopped after the fourth week for the analysis of disease relapse. Leukemic cell analysis from peripheral blood in the fifth and seventh week clearly demonstrated that the mice treated with single and two drugs relapsed, while triple drug treatment had no sign of leukemic cells in peripheral blood. These results suggested that mice in this treatment group were cured of the disease.

Given the problems associated with curcumin absorption and bioavailability, other c-FOS inhibitors were evaluated. The c-fos inhibitors nordihydroguaiaretic acid (NDGA) and difluorinated curcumin (DFC) were tested in two different mouse models of leukemia, namely, retroviral-bone marrow transplant model, and a BCR/ABL transgenic mouse model that allows expression of BCR/ABL only in primitive and multiprogenitors (MPPs) hematopoietic stem cells. Assessing efficacy of these drug combinations in transgenic mouse models permitted analysis of LSC dynamics and survival, and provided definitive proof for eradication of LSCs.

The data demonstrated that a combination of DFC, BCI, and Imatinib was more potent than combinations with curcumin, BCI, and Imatinib, and with NDGA, BCI, and Imatinib, as shown in FIGS. 6 and 7A-D.

Figure 6:
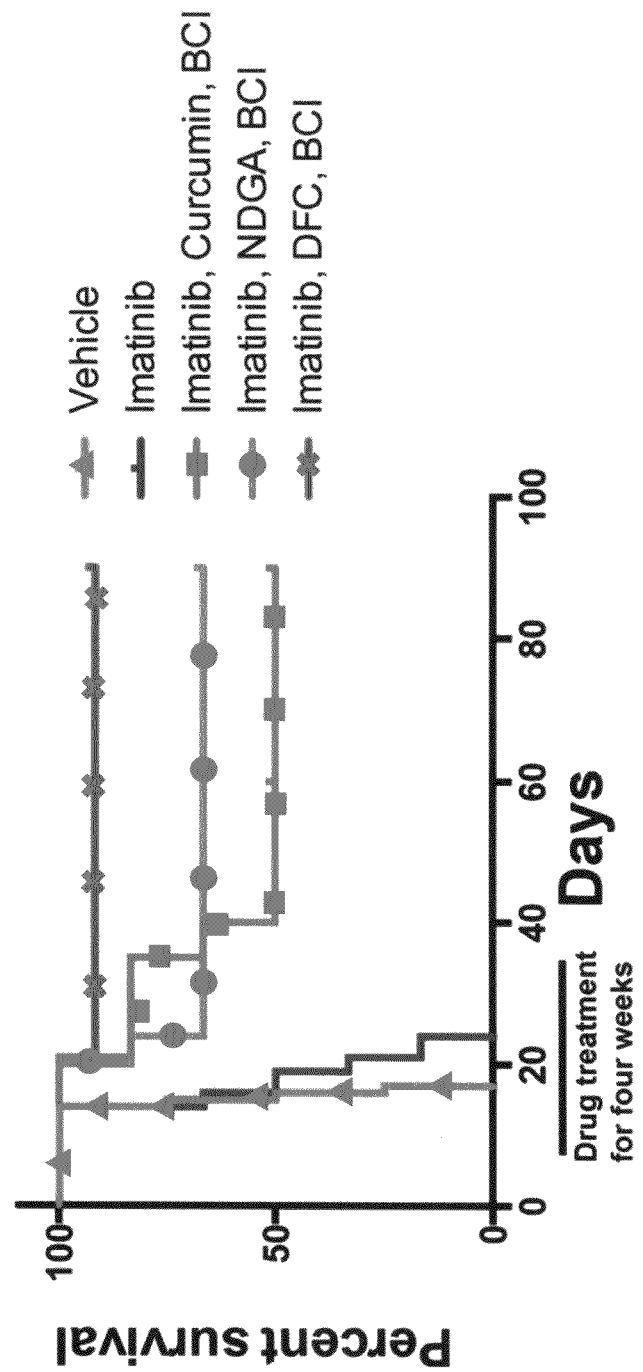
FIG. 6 demonstrates efficacy of compositions in curing mice with leukemia in retroviral-transduction bone marrow transplantation mouse model of chronic myelogenous leukemia (CML).
Figure 7A:
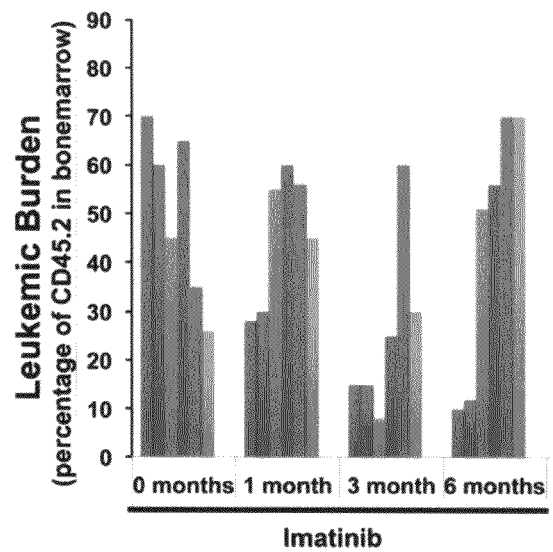
FIGS. 7A-D demonstrate ability of inventive compositions to eradicate leukemic stem cells from SCL-BCR/ABL-mice.
Figure 7B:
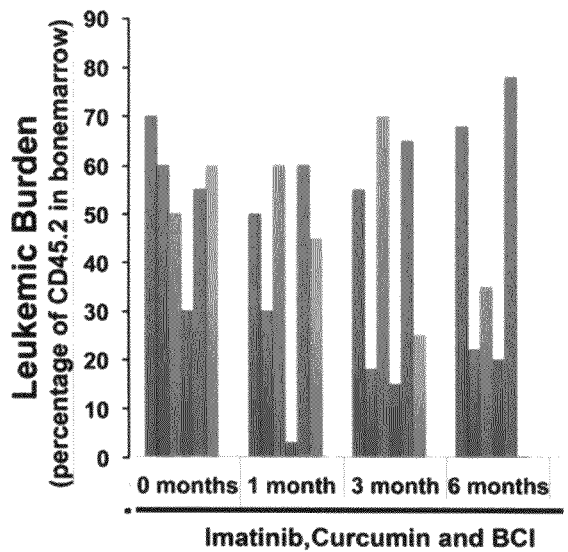
Figure 7C:
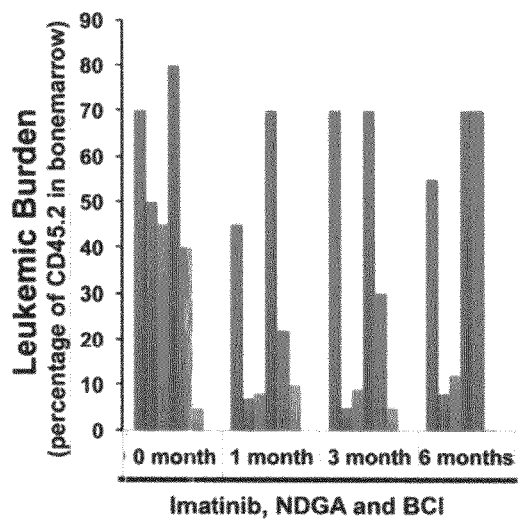
Figure 7D:
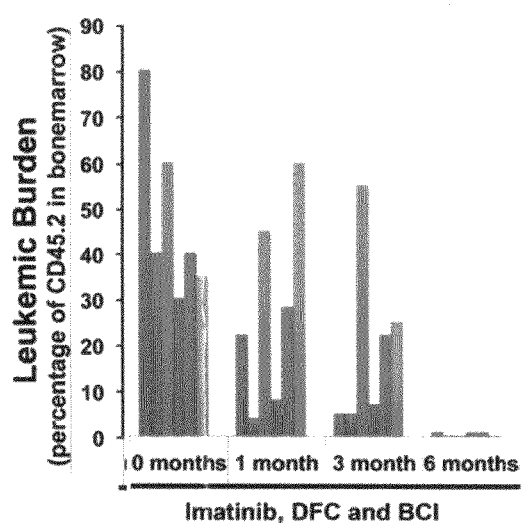

FIG. 6 shows that the combination of Imatinib, DFC and BCI was more effective in curing the mice from leukemia in retroviral-transduction bone marrow-transplantation mouse model of CML. Briefly, c-Kit positive bone marrow cells were harvested from wild type mice and transduced with retroviruses expressing BCR/ABL followed with transplantation of 100,000 transduced cell in each mice with 1 million normal bone marrow cells. In this model, mice develop leukemia within two weeks and all mice die within three to four weeks.

All three combinations, namely DFC, BCI, and Imatinib; curcumin, BCI, and Imatinib; and NDGA, BCI, and Imatinib, cured mice from the disease. DFC, BCI, and Imatinib was most effective in curing mice from the disease. While not being bound by a single theory, the greater efficacy of DFC, BCI, and Imatinib was likely due to DFC's greater bioavailability and binding with c-Fos.

FIGS. 7A-D show that the combination of Imatinib, DFC and BCI completely eradicated the leukemic stem cells from the SCL-BCR/ABL mice. Briefly, bone marrow cells were harvested from the SCL-BCR/ABL mice and transplanted in Boy/J mice with equal amount of BM cells from the Boy/J mice. After one month, transplantation chimerism was recorded by measuring the percentage of CD45.2 (BCR/ABL) from the bone marrow aspirates which is labeled as 0 month. After one-month drug treatments were started, and leukemic burdens were monitored by measuring the levels of CD45.2. As shown in FIGS. 7A-D, the combination of Imatinib, DFC and BCI completely cured the mice.

In vivo data unequivocally demonstrated that Dusp-1 and c-Fos mediated BCR-ABL addiction and leukemic stem cell biology. Dusp-1 and c-Fos inhibitors are thus targets for curative therapy in CML.

Each of the following references is expressly incorporated by reference herein in its entirety:

Aikawa et al. "Treatment of arthritis with a selective inhibitor of c-Fos/activator protein-1," Nature Biotechnology, vol. 26, no. 7 (2008), pp. 817-823.

Day et al., "Small Molecule Inhibitors of DUSP6 and Uses Therefor," WO2010/108058, Sep. 23, 2010.

Park et al., "Inhibition of fos-jun-DNA complex formation by dihydroguaiaretic acid and in vitro cytotoxic effects on cancer cells," Cancer Letters, vol. 127 (1998), pp. 23-28.

Padhye S, et al. New difluoro Knoevenagel condensates of curcumin, their Schiff bases and copper complexes as proteasome inhibitors and apoptosis inducers in cancer cells. Pharm Res 2009; 26:1874-80.

Padhye S et al. Fluorocurcumins as cyclooxygenase-2 inhibitor: molecular docking, pharmacokinetics and tissue distribution in mice. Pharm Res. 2009 November; 26(11): 2438-45.

Other variations or embodiments will be apparent to a person of ordinary skill in the art from the above description. Thus, the foregoing embodiments are not to be construed as limiting the scope of the claimed invention.

What is claimed is:

1. A method of curative therapy for chronic myelogenous leukemia (CML) in a patient, the method comprising administering to the patient in need thereof a composition containing at least one biocompatible excipient and, as the only active agents, a combination of
    (a) an inhibitor of c-Fos resulting in inhibition of c-Fos,
    (b) an inhibitor of Dusp-1 resulting in inhibition of Dusp-1, and
    (c) an inhibitor of BCR-ABL tyrosine kinase resulting in inhibition of BCR-ABL tyrosine kinase, the composition administered to the patient in a dosing regimen for a period sufficient to provide curative therapy for chronic myelogenous leukemia to the patient in need thereof.

2. The method of claim 1 where (a) is an inhibitor of a c-Fos gene, (b) is an inhibitor of a Dusp-1 gene, and (c) is an inhibitor of a BCR-ABL tyrosine kinase gene.

3. The method of claim 1 where (a) is an inhibitor of a c-Fos protein, (b) is an inhibitor of a Dusp-1 protein, and (c) is an inhibitor of a BCR-ABL tyrosine kinase protein.

4. The method of claim 1 where (a) is selected from the group consisting of curcumin, difluorinated curcumin (DFC), [3-{5-[4-(cyclopentyloxy)-2-hydroxpenzoyl]-2-[(3-hydroxy-1,2-benzisoxazol-6-yl) methoxy]phenyl}propionic acid] (T5224), nordihydroguaiaretic acid (NDGA), dihydroguaiaretic acid (DHGA), [(E,E,Z,E)-3-methyl-7-(4-methylphenyl)-9-(2,6,6-trimethyl-1-cyclohexen-1-yl)-2,4,6,8-nonatetraenoic acid (SR11302), and combinations thereof; (b) is selected from the group consisting of (E)-2-benzylidene-3-(cyclohexylamino)-2,3-dihydro-1H-inden-1-one (BCI), TPI-2, TPI-3, triptolide, and combinations thereof; and (c) is selected from the group consisting of Imatinib, Nilotinib, Dasatinib, Ponatinib, and combinations thereof.

5. The method of claim 4 where (a) is curcumin, (b) is BCI; and (c) is Imatinib.

6. The method of claim 4 where (a) is NDGA, (b) is BCI; and (c) is Imatinib.

7. The method of claim 4 where (a) is T5224, (b) is BCI; and (c) is Imatinib.

8. The method of claim 4 where (a) is difluorinated curcumin (DFC), (b) is BCI; and (c) is Imatinib.

9. The method of claim 1 where (a) is administered at a concentration of 2 grams per day to 8 grams per day, inclusive; (b) is administered at a concentration of 100 mg per day to 600 mg per day, inclusive; and (c) is administered at a concentration of 400 mg per day to 800 mg per day, inclusive.

10. The method of claim 1 where the composition is administered to the patient for 30 days.

11. The method of claim 1 where the composition is administered to the patient intravenously, orally, transdermally, intramuscularly, and/or intraperitoneally to result in an effective dosing regimen.

12. The method of claim 1 where the composition is administered as a cocktail.

13. A pharmaceutically acceptable composition comprising at least one biocompatible excipient and, as the only active agents, Imatinib, (E)-2-benzylidene-3-(cyclohexylamino)-2,3-dihydro-1H-inden-1-one (BCI), and nordihydroguaiaretic acid (NDGA), or difluorinated curcumin (DFC).

14. The composition of claim 13 where the concentration of Imatinib is 400 mg per day to 800 mg per day, inclusive; the concentration of BCI is 100 mg per day to 600 mg per day, inclusive; and the concentration of nordihydroguaiaretic acid (NDGA), or difluorinated curcumin (DFC) is 2 grams per day to 8 grams per day, inclusive.

15. A method of providing therapy to a patient with chronic myelogenous leukemia comprising administering to the patient with leukemia a composition containing a combination of at least one inhibitor for each of a c-Fos gene and/or protein resulting in inhibition of the c-Fos gene and/or protein, a Dusp-1 gene and/or protein resulting in inhibition of the Dusp-1 gene and/or protein, and a BCR-ABL tyrosine kinase gene and/or protein resulting in inhibition of the BCR-ABL gene and/or protein, the composition administered to the patient in a dosing regimen sufficient to eliminate leukemia initiating cells from the patient's blood.

16. A method of curative therapy for chronic myelogenous leukemia by preparing a composition and administering to a patient in need thereof, the composition containing as its only active agents at least one of each of at least one inhibitor of a c-Fos gene and/or protein resulting in inhibition of the c-Fos gene and/or protein, at least one inhibitor for a Dusp-1 gene and/or protein resulting in inhibition of the Dusp-1 gene and/or protein, and at least one inhibitor for a BCR-ABL tyrosine kinase gene and/or protein resulting in inhibition of the BCR-ABL gene and/or protein; Dusp-1, c-Fos, and BCR-ABL tyrosine kinase being targets for curative therapy in chronic myelogenous leukemia.

17. The method of claim 16 where the c-Fos inhibitor is selected from the group consisting of curcumin, difluorinated curcumin (DFC), [3-{5-[4-(cyclopentyloxy)-2-hydroxybenzoyl]-2-[(3-hydroxy-1,2-benzisoxazol-6-yl)methoxy]phenyl}propionic acid] (T5224), nordihydroguaiaretic acid (NDGA), dihydroguaiaretic acid (DHGA), [(E,E,Z,E)-3-methyl-7-(4-methylphenyl)-9-(2,6,6-trimethyl-1-cyclohexen-1-yl)-2,4,6,8-nonatetraenoic acid (SR11302), and combinations thereof; the Dusp-1 inhibitor is selected from the group consisting of (E)-2-benzylidene-3-(cyclohexylamino)-2,3-dihydro-1H-inden-1-one (BCI), TPI-2, TPI-3, triptolide, and combinations thereof; and the BCR-ABL tyrosine kinase inhibitor is selected from the group consisting of Imatinib, Nilotinib, Dasatinib, Ponatinib, and combinations thereof.

18. A pharmaceutically acceptable composition comprising at least one biocompatible excipient and, as the only active agents, (a) a c-Fos inhibitor resulting in inhibition of the c-Fos, (b) a Dusp-1 inhibitor resulting in inhibition of the Dusp-1, and (c) a BCR-ABL tyrosine kinase inhibitor resulting in inhibition of the BCR-ABL.

19. The pharmaceutically acceptable composition of claim 18 wherein,
   (a) the c-Fos inhibitor is selected from the group consisting of curcumin, difluorinated curcumin (DFC), [3-{5-[4-(cyclopentyloxy)-2-hydroxybenzoyl]-2-[(3-hydroxy-1,2-benzisoxazol-6-yl) methoxy]phenyl}propionic acid] (T5224), nordihydroguaiaretic acid (NDGA), dihydroguaiaretic acid (DHGA), and [(E,E,Z,E)-3-methyl-7-(4-methylphenyl)-9-(2,6,6-trimethyl-1-cyclohexen-1-yl)-2,4,6,8-nonatetraenoic acid (SR11302);
   (b) the Dusp-1 inhibitor is selected from the group consisting of (E)-2-benzylidene-3-(cyclohexylamino)-2,3-dihydro-1H-inden-1-one (BCI—also known as NSC 150117), TPI-2, TPI-3, and triptolide; and
   (c) the BCR-ABL tyrosine kinase inhibitor is selected from the group consisting of Imatinib mesylate (Gleevec™), Nilotinib, Dasatinib and Ponatinib.

20. A pharmaceutically acceptable composition comprising at least one biocompatible excipient and, as the only active agents, Imatinib, (E)-2-benzylidene-3-(cyclohexylamino)-2,3-dihydro-1H-inden-1-one (BCI), and difluorinated curcumin (DFC).

* * * * *

UNITED STATES PATENT AND TRADEMARK OFFICE
CERTIFICATE OF CORRECTION

PATENT NO. : 9,877,934 B2  
APPLICATION NO. : 14/048806  
DATED : January 30, 2018  
INVENTOR(S) : Mohammad Azam and Meenu Kesarwani Page 1 of 1

It is certified that error appears in the above-identified patent and that said Letters Patent is hereby corrected as shown below:

In Claim 4, at Column 10, Line 51 reads:  
"(DFC), [3-{5-[4-(cyclopentyloxy)-2-hydroxpenzoyl]-2-[(3-"  
It should read:  
--(DFC), [3-{5-[4-(cyclopentyloxy)-2-hydroxybenzoyl]-2-[(3- --

Signed and Sealed this  
Twenty-ninth Day of May, 2018

Andrei Iancu  
*Director of the United States Patent and Trademark Office*